(12) United States Patent
Cleary et al.

(10) Patent No.: US 6,355,255 B1
(45) Date of Patent: Mar. 12, 2002

(54) STREPTOCOCCAL C5A PEPTIDASE VACCINE

(75) Inventors: Paul Patrick Cleary, Shoreview; Deborah K. Stafslien, Fridley, both of MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/206,898

(22) Filed: Dec. 7, 1998

Related U.S. Application Data

(63) Continuation-in-part of application No. 08/589,756, filed on Jan. 22, 1996, now Pat. No. 5,846,547.

(51) Int. Cl.[7] .................... A61K 39/385; A61K 39/295; A61K 39/85; A61K 39/09; A61K 39/02

(52) U.S. Cl. ............................... 424/244.1; 424/197.11; 424/200.1; 424/237.1; 424/244.1; 424/823; 424/825; 424/828; 424/829; 435/7.34; 435/24; 435/36; 435/93.44; 435/165.1; 435/216; 435/219; 435/253.4; 435/340; 530/388.4

(58) Field of Search ................ 424/197.11, 200.1, 424/237.1, 244.1, 823, 825, 828, 829; 435/7.34, 24, 36, 93.44, 165.1, 216, 219, 253.4, 340; 530/388.4

(56) References Cited

U.S. PATENT DOCUMENTS

| | | | |
|---|---|---|---|
| 4,454,121 A | 6/1984 | Beachey | 424/177 |
| 4,695,562 A | 9/1987 | Beachey et al. | 514/13 |
| 4,772,584 A | 9/1988 | Cleary et al. | 419/2 |
| 5,124,153 A | 6/1992 | Beachey et al. | 424/93 P |
| 5,162,226 A | 11/1992 | Beachey et al. | 435/252.3 |
| 5,846,547 A | * 12/1998 | Cleary | 424/244.1 |

FOREIGN PATENT DOCUMENTS

| | | | | |
|---|---|---|---|---|
| AU | WO 93/21220 | * 10/1993 | ............ | C07K/7/08 |
| EP | 94/06421 | 3/1994 | | |
| EP | 94/06465 | 3/1994 | | |
| EP | WO 95/28960 | * 11/1995 | .......... | A61K/39/09 |
| WO | WO 89/09063 | * 10/1989 | .......... | A61K/39/02 |
| WO | 89/09064 | 10/1989 | | |
| WO | 93/14198 | 7/1993 | | |
| WO | 93/21220 | 10/1993 | | |
| WO | 94/06421 | 3/1994 | | |
| WO | 94/06465 | 3/1994 | | |
| WO | 95/28960 | 11/1995 | | |
| WO | 97/26008 | 1/1996 | .......... | A61K/39/09 |

OTHER PUBLICATIONS

Wexkler et al. 1985. PNAS. 82: 8144–8148, 1985.*
O'Conner et al. 1987. J. of Infect. Diseases. 156(3): 495–503, 1987.*
Bessen et al. 1988. Infection and Immunity. 56(10): 2666–2672, 1988.*
Hill et al. 1988. J. of Immuno. 141(10): 3351–3556, 1988.*
Chen et al. 1900. J. of Biol. Chem. 265(6): 316–3167, 1990.*
Cleary et al. 1991. Infect. and Immunol. 59(7): 2305–2310, 1991.*

(List continued on next page.)

*Primary Examiner*—Lynette R. F. Smith
*Assistant Examiner*—Jana A. Hines
(74) *Attorney, Agent, or Firm*—Schwegman, Lundberg, Woessner & Kluth, P.A.

(57) ABSTRACT

Novel vaccines for use against β-hemolytic Streptococcus colonization or infection are disclosed. The vaccines contain an immunogenic amount of a variant of strepococcal C5a peptidase (SCP). Also disclosed is a method of protecting a susceptible mammal against β-hemolytic Streptococcus colonization or infection by administering such a vaccine. Enzymatically inactive SCP, and polynucleotides encoding these SCP proteins are further disclosed.

29 Claims, 13 Drawing Sheets

OTHER PUBLICATIONS

Berge et al. 1995. J. of Biol. Chem. 270(17): 9862–9867, 1995.*

Cleary et al. 1992. Infect. and Immun. 60(10): 4239–4244, 1992.*

Cleary et al., 1992. Infect. and Immun. 60(12): 5219–5223, 1992.*

Bessen, D., et al., "Synthetic Peptide Vaccine Against Mucusal Colonization by Group A Streptococci. I. Protection Against a Heterologous M Serotype with Shared C Repeat Region Epitopes", *J. Immunol*, 145(4), 1251–1256, (1990).

Cleary, P., et al., "Streptococcal C5a Peptidase is a Highly Specific Endopeptidase", *Infection and Immunity*, 60(12), 5219–5223, (1992).

Carter, P., et al., "Dissecting the catalytic triad of a serine protease", *Nature,* vol. 3323, XP002135964, 564–568, (Apr. 7, 1988).

Stafslien, D.K., et al., "Site Directed Mutagenesis of the Streptococcal C5a Peptidase", *Abstracts of the General Mtg of the Am. Soc for Microbiology,* vol. 98, XP002135963, 59, (May, 1998).

Berg, A., et al., "Streptococcal Cysteine Proteinase Releases Biologically Active Fragments of Streptococcal Surface Proteins", *The Journal Of Biological Chemistry,* vol. 270, No. 17, 9862–9867, (Apr. 28, 1995).

Bessen, D., et al., "Influence of Intranasal Immunization with Synthetic Peptides Corresponding to Conserved Epitodes of M Protein on Mucosal Colonization by Group A Streptococci", *Infection and Immunity,* 56, 2666–2672, (Oct. 1988).

Bessen, D., et al., "Synthetic peptide vaccine against mucosal colonization by group A Streptococci", *J. Immunol.,* 145, 1251–1256, (1990).

Booth, S., et al., "Dapsone Suppresses Integrin–Mediated Neutrophil Adherence Function", *The Journal of Investigative Dermatology,* 98, 135–140, (Feb. 1992).

Boyle, M., et al., "Measurement of Leukocyte Chemotaxis in Vivo", *Methods in Enzymology,* 162, 101–114, (1988).

Bronze, M., et al., "Epitopes of group A streptococcal M protein that evoke cross–protective local immune responses", *J. Immunol.,* 148, 888–893.

Bronze, M., et al., "Protective Immunity Evoked by Locally Administered Group A Streptococcal Vaccines in Mice", *J. Immunol.,* 141, 2767–2770, (10/88).

Brummer, E., et al., "Immunological Activation of Polymorphonuclear Neutrophils for Fungal Killing: Studies with Murine Cells and *Blastomyces Dermatitidis* In Vitro", *Journal of Leukocyte Biology,* 36, 505–520, (1984).

Chen, C.C., et al., "Complete Nucleotide Sequence of the Streptococcal C5A Peptidase Gene of *Streptococcus pyogenes*", *The Journal of Bilogical Chemistry,* vol. 265, No. 6, pp. 3161–3167, (Feb. 25, 1990).

Clark, J., et al., "A New Method for Quantitation of Cell–Mediated Immunity in the Mouse", *Journal of the Reticuloendothelial Society,* 25, 255–267, (Mar. 1992).

Cleary, P., et al., "A Streptococcal Inactivator of Chemotaxis: A new Virulence Factor Specific to Group A Streptococci", Recent Advances in Streptococci and Streptococcal Diseases (Y. Kimura, S. Kotami and Y. Shiokawa (ed). Reedbooks, ltd; Berkshire, England, 179–180, (1984).

Cleary, P., et al., "Streptococcal C5a Peptides is a Highly Specific Endooeptidase Genes", *Infection and Immunity,* 60, 4239–4244, (Oct. 1992).

Cleary, P., et al., "Virulent Human Strains of Group G Streptococci Express a C5a Peptidase Enzyme Similar to that Produced by a Group A Streptococci", *Infection and Immunity,* 59, 2305–2310, (Jul. 1991).

Cleary, P.P., et al., "Similarity between the Group B and A streptococcal C5a Peptidase Genes", *Infection and Immunity,* vol. 60, No. 10, pp. 4239–4244, (Oct. 1992).

Courtney, H.S., et al., "Analysis of the role of M24 Protein in group A Streptococcal adhesion and colonization by use of 'omega'–interposon mutagenesis", *Infect. Immun.,* 62, 4868–4873, (1994).

Fenderson, P., et al., "Tropomysin Shares immunology Epitopes with Group A Streptococcal M Proteins", *The Journal of Immunology,* 142, 2475–2482, (Apr. 1989).

Fischetti, V., "Streptococcal M Protein: Molecular Designn and Biological Behavior", *Clinical Microbiology Reviews,* 2, 285–314, (Jul. 1989).

Fischetti, V.A., et al., "Protection against streptococcal pharyngeal colonization with vaccines composed of M protein conserved regions", *Plenum Press.,* 159–167, (1991).

Fischetti, V.A., et al., "Protection against streptococcal pharyngeal colonization with a vacine: M protein recombinant", *Science,* 244, 1487, (1989).

Hill, H., et al., "Group B Streptococci Inhibit the Chemotactic Activity of the Fifth Component of Complement", *The Journal of Immunology,* 141, 3551–3556, (Nov. 1988).

Hope–simpson, R., "*Streptococcus Pyogenes* in the Throat: A study in a small population, 1962–1975", *J. Hyg. Camb.,* 87, 109–129, (1981).

Ji, Y., et al., "C5a peptidase alters clearance and trafficking of a group A streptococci by infected mice", *Infect. Immun.,* 64, 503–510, (1996).

Ji, Y., et al., "Intranasal immunization with C5a peptidase prevents nasopharyngeal colonization of mice by the group A streptococcus", *Infect. Immun.,* 65, 2080–2087, (1997).

Kapur, V., et al., "Vaccination with streptococcal extracellular cysteine protease (interleukin–1B convertase) protects mice against challenge with heterologous group A streptococci", *Microbial. Path.,* 16, 443–459, (1994).

Laemmli, U.K., "Cleavage of Structural Proteins during the Assembly of the Head of Bacteriophage T4", *Nature,* 227, 680–685, (Aug., 1970).

Lee, P., et al., "Quantification and Toxicity of a Group A Streptococcal Pyrogenic Exotoxins in an Animal Model of Toxic Shock Syndrome–Like Illness", *Journal of Clinical Microbiology,* 27, 1890–1892, (Aug. 1989).

Martin, T., et al., "The Effect of Type–Specific Polysaccharide Capsule on the Clearance of Group B Streptococci from the Lungs of Infant and Adult Rats", *The Journal of Infectious Diseases,* 165, 306–314, (Feb. 1992).

Massell, B., et al., "Rheumatic Fever Following Streptococcal Vaccination", *JAMA,* 207, 1115–1119, (Feb. 1969).

Mcghee, J., et al., "New Perspective in Mucosal Immunity with Emphasis on Vaccine Development", *Seminars in Hematology,* 30, 3–15, (Oct. 1993).

Medaglini, D., et al., "Mucosal and systemic immune responses to a recombinant protein expressed on the surface of the oral commensal bacterium *Streptococcus gordonii* after oral colonization", *Proc. Natl. Acad. Sci. USA,* 6868–6872, (1995).

O'connor, S., et al., "In Vivo *Streptococcus Pyogenes* C5a Peptidase Activity: Analysis Using Transposon– and Nitrosoguanidine– Induced Mutants", *The Journal of Infectious Disease,* 156, 459–504, (Sep. 1987).

O'connor, S., et al., "The Human Antibody Response to Streptococcal C5a Peptidase", *The Journal of Infection Diseases,* 163, 109–116, (Jan. 1991).

Pidbielski, A., et al., "The Group A Streptococcal VirR49 Gene Controls Expression of Four Structural Vir Regulon Genes", *Infection and Immunity,* 63, 9–20, (Jan. 1995).

Raeder, R., et al., "Properties of IgG–binding proteins expressed by *Streptococcus pyogenes* isolates are predictive of invasive potential", *J. Infect. Dis.,* 173, 888–895, (1996).

Springer, T., et al., "Mac–1: A Macrophage Differentiation Antigen Identified by Monoclonal Antibody", *European Journal of Immunology,* 9, 301–306, (1979).

Sriskandan, S., et al., "Streptococcal pyrogenic exotoxin A (SPEA) release, distribution, and role in a murine model of fasciitis and multi–organ failure due to *Streptococcus pyogenes*", *J. Infect. Dis.,* 173, 1399–1407, (1996).

Sriskandan, S., et al., "The role of nitric oxide in experimental murine sepsis due to pyrogenic exotoxin A–producing *Streptococcus pyogenes*", *Infect. Immun.,* 65, 1767–1762, (1997).

Stevens, D., "Invasive Group A Streptococcus Infections", *Clinical Infectious Diseases,* 14, 2–13, (Jan. 192).

Suvorov, A., et al., "C5a Peptidase Gene from Group A Streptococci", *Genetics and Molecular Biology of Streptococci, Lactococci, and Enterococci,* G. Washington, D.C., 230–232, (1991).

Vugia, D.J., et al., "Invasive group A streptococcal infections in children with varicella in Southern California", *Pediatr. Infect. Dis. J.,* vol. 15, No. 2, 146–150, (1996).

Wessels, M., et al., "Critical role of the group A streptococcal capsule in pharnygeal colonization and infection in mice", *Proc. Natl. Sci. USA,* 91, 12238–12242, (1994).

Wexler, D., et al., "Mechanism of Action of the Group A Streptococcal C5a Inactivator", *Proc. Natl. Acad. Sci.* 82, 8144–8148, (Dec. 1985).

\* cited by examiner

```
          1                                                           ▽
          LRKKQKLPFDKLAIALMSTSILLNAQSDIKANTVTEDTPATEQAVETPQPTTVSEEVPSS
SCPA49    ------------------------------------------V-----A----------
SCPA12    ----------------------------------------T-------A---A------
SCPB      ------------------------------------------------A---A------
SCPA1

61
          KETKTPQTPDDAEETVADDANDLAPQAPAKTPDTSATSKATIRDLNDPSQVKTLQEKAGK
          ------I-----------------------A--P--------------------------
          ---S--G-------------------------A--P------------------------
          ------I-------------------A--P------------------------------

121       *
          GAGTVVAVIDAGFDKNHEAWRLTDKAKARYQSKEDLEKAKKEHGITYGEWVNDKVAYYHD
          ------------------------T-----------------------------------
          ------------------------T-----------------------------------
          ------------------------T-----------------------------------

181                     *
          YSKDGKTAVDQEHGTHVSGILSGNAPSETKEPYRLEGAMPEAQLLLHRVEIVNGLADYAR
          ------------------------------------------------------------
          ------------------------------------------------------------
          ------------------------------------------------------------

241                                                         *
          NYAQAIRDAVNLGAKVINMSFGNAALAYANLPDETKKAFDYAKSKGVSIVTSAGNDSSFG
          -----I------------------------------------------------------
          ------------------------------------------------------------
          -----I------------------------------------------------------
```

FIG. 2A

```
301 GKTRLPLADHPDYGVVGTPAAADSTLTTVASYSPDKQLTETATVKTADKQDKEMPVLSTNR
                                          --M---D-Q-
                                          --VR-----Q-
                                                   -Q-

361 FEPNKAYDYAYANRGMKEDDFKDVKGKIALIERGDIDFKDKIANAKKAGAVGVLIYDNQD
                     -T-                  -V-
                                                   -K-

421 KGFPIELPNVDQMPAAFISRKDGLLLKDNSKKTITFNATPKVLPTASGTKLSRFSSWGLT
                                PQ-
                                PQ-
                              -E-PQ-

481 ADGNIKPDIAAPCRDILSSVANNKYAKLSGTSMSAPLVAGIMGLLQKQYETQYPDMTPSE
                                *
    --GQ-
    --GQ-
    --GQ-

541 RLDLAKKVLMSSATALYDEDEKAYFSPRQQGAGAVDAKKASAATMYVTDKDNTSSKVHLN
```

FIG. 2B

```
601 NVSDKFEVTVTVHNKSDKPQELYYQATVQTDKVDGKHFALAPKALYETSWQKITIPANSS
    ------------N---------------------V---A---------------------
    --------------------------------------V---A-----------------
    ----------------------------------L-------------------------
    ------------------------------------------------------------
    ------------------------------------------------------------
    ------------------------------------------------------------

661 KQVTIPIDASQFSKDLLAQMKNGYFLEGFVRFKQDPTKEELMSIPYIGFRGDFGNLSALE
    ----V----R--------------------------------------------------
    ----V----R--------------------K-----------------------------V
    --------V------P--------------------------------------------
    ------------------------------------------------------------
    ------------------------------------------------------------

721 KPIYDSKDGSSYYHEANSDAKDQLDGDGLQFYALKNNFTALTTESNPWTIIKAVKEGVEN
    ------------------------------------------------------------
    ------------------------------------------------------------
    ------------------------------------------------------------
    ------------------------------------------------------------
    ------------------------------------------------------------

781 IEDIESSEITETIFAGTFAKQDDDSHYYIHRHANGKPYAAISPNGDGNRDYVQFQGTFLR
    ----------------------------------E-------------------------
    -------------L----------------------------------------------
    ------------------------------------------------------------
    ------------------------------------------------------------
    ------------------------------------------------------------

841 NAKNLVAEVLDKEGNVVWTSEVTEQVVKNYNNDLASTLGSTRFEKTRWDGKDKDGKVVAN
    ------------------------------------------------------------
    ------------------------------------------------------------
    ------------------------------------------------------------
    ------------------------------------------------------------
```

FIG. 2C

```
901
    GTYTYRVRYTPISSGAKEQHTDFDVIVDNTTPEVATSATFSTEDRRLTLASKPKTSQPVY
    ------------------------------------------------------------
    ------------------------------------------------------------
961
    RERIAYTYMDEDLPTTEYISPNEDGTFTLPEEAETMEGATVPLKMSDFTYVVEDMAGNIT
    ----------------------------------T-------------------------
    ------------------------------------------------------------
1021
    YTPVTKLLEGHSNKPEQDGS DQAPDKKPETKPEQDGS DQAPDKKPETKPEQDGSGQTPDK
    -------------------- G-T----------A-- ----------A-----------
    -------------------- ................ --------------G-------
1081
    KPETKPEKDSSGQTPGKTPQKGQPSRTLEKRSSKRALATKASTRDQLPTTNDKDTNRLHL
    -T----------------------------------------------------------
    -------Q-G----------------------------------K---------------
1141
    LKLVMTFFFLGLVAHIFKTKR ...TED
    -------F------------ QKE-KK
    -------------------- QKE-KK
```

FIG. 2D

Thr⁶³ OR T⁶³        His¹⁰³¹ OR H¹⁰³¹

| SIGNAL | | CELL WALL ANOCHOR |
|---|---|---| scpA For1033 →     ← scpA Rev3941

FRAGMENT SUBCIONED

⇩ pGEX-4T-1 EXPRESSION VECTOR GIUTATHIONE-SCPA49 FUSION

⇩

AFFINITY PURIFATION-GLUTATHIONE COLUMN

⇩

INTRANASAL INOCULATION
(FIVE 40μg DOSES)

FIG. 7

SEQUENCE LISTING

<160> NUMBER OF SEQ ID NOS: 23

<210> SEQ ID NO 1
<211> LENGTH: 1164
<212> TYPE: PRT
<213> ORGANISM: Streptococcus pyogenes

<400> SEQUENCE: 1

```
Leu Arg Lys Lys Gln Lys Leu Pro Phe Asp Lys Leu Ala Ile Ala Leu
 1               5                  10                  15

Met Ser Thr Ser Ile Leu Leu Asn Ala Gln Ser Asp Ile Lys Ala Asn
            20                  25                  30

Thr Val Thr Glu Asp Thr Pro Ala Thr Glu Gln Ala Val Glu Thr Pro
        35                  40                  45

Gln Pro Thr Thr Val Ser Glu Glu Val Pro Ser Lys Glu Thr Lys
    50                  55                  60

Thr Pro Gln Thr Pro Asp Asp Ala Glu Glu Thr Val Ala Asp Asp Ala
65                  70                  75                  80

Asn Asp Leu Ala Pro Gln Ala Pro Ala Lys Thr Pro Asp Thr Ser Ala
                85                  90                  95

Thr Ser Lys Ala Thr Ile Arg Asp Leu Asn Asp Pro Ser Gln Val Lys
            100                 105                 110

Thr Leu Gln Glu Lys Ala Gly Lys Gly Ala Gly Thr Val Val Ala Val
        115                 120                 125

Ile Asp Ala Gly Phe Asp Lys Asn His Glu Ala Trp Arg Leu Thr Asp
130                 135                 140

Lys Ala Lys Ala Arg Tyr Gln Ser Lys Glu Asp Leu Glu Lys Ala Lys
145                 150                 155                 160

Lys Glu His Gly Ile Thr Tyr Gly Glu Trp Val Asn Asp Lys Val Ala
                165                 170                 175

Tyr Tyr His Asp Tyr Ser Lys Asp Gly Lys Thr Ala Val Asp Gln Glu
            180                 185                 190

His Gly Thr His Val Ser Gly Ile Leu Ser Gly Asn Ala Pro Ser Glu
        195                 200                 205

Thr Lys Glu Pro Tyr Arg Leu Glu Gly Ala Met Pro Glu Ala Gln Leu
    210                 215                 220

Leu Leu Met Arg Val Glu Ile Val Asn Gly Leu Ala Asp Tyr Ala Arg
225                 230                 235                 240

Asn Tyr Ala Gln Ala Ile Arg Asp Ala Val Asn Leu Gly Ala Lys Val
                245                 250                 255

Ile Asn Met Ser Phe Gly Asn Ala Ala Leu Ala Tyr Ala Asn Leu Pro
            260                 265                 270

Asp Glu Thr Lys Lys Pro Phe Val Tyr Ala Lys Ser Lys Gly Val Arg
        275                 280                 285

Ile Val Thr Thr Ala Gly Asn Asp Ser Ser Phe Gly Gly Lys Thr Arg
    290                 295                 300

Leu Pro Leu Ala Asp His Pro Asp Tyr Gly Val Gly Thr Pro Ala
305                 310                 315                 320

Ala Ala Asp Ser Thr Leu Thr Val Ala Ser Tyr Ser Pro Asp Asn Gln
                325                 330                 335

Leu Thr Glu Thr Ala Met Val Lys Thr Asp Asp Gln Asp Lys Glu
            340                 345                 350

Met Pro Val Leu Ser Thr Asn Arg Phe Glu Pro Asn Lys Ala Tyr Asp
```

-continued

```
            355                 360                 365
Tyr Ala Tyr Ala Asn Arg Gly Met Lys Glu Asp Asp Phe Lys Asp Val
            370                 375                 380
Lys Gly Lys Ile Ala Leu Ile Glu Arg Ser Asp Ile Asp Phe Thr Asp
385                 390                 395                 400
Lys Ile Ala Asn Ala Lys Lys Ala Gly Ala Val Gly Val Leu Ile Tyr
                405                 410                 415
Asp Asn Gln Asp Lys Gly Phe Pro Ile Glu Leu Pro Asn Val Asp Gln
                420                 425                 430
Met Pro Ala Ala Phe Ile Ser Arg Lys Asp Gly Leu Leu Leu Lys Asp
            435                 440                 445
Asn Ser Gln Lys Thr Ile Thr Phe Asn Ala Thr Pro Lys Val Leu Pro
450                 455                 460
Thr Ala Ser Gly Thr Lys Leu Ser Arg Phe Ser Ser Trp Gly Leu Thr
465                 470                 475                 480
Ala Asp Gly Asn Ile Lys Pro Asp Ile Ala Ala Pro Gly Gln Asp Ile
                485                 490                 495
Leu Ser Ser Ala Ala Asn Asn Lys Tyr Ala Lys Leu Ser Gly Thr Ser
            500                 505                 510
Met Ser Ala Pro Leu Val Ala Val Ile Met Gly Leu Leu Gln Lys Gln
            515                 520                 525
Tyr Glu Thr Gln Tyr Pro Asp Met Thr Gln Ser Glu Arg Leu Asp Leu
530                 535                 540
Ala Lys Lys Val Leu Met Ser Ser Ala Thr Ala Leu Tyr Asp Glu Asp
545                 550                 555                 560
Glu Lys Ala Tyr Phe Ser Pro Arg Gln Gln Gly Ala Gly Ala Val Asp
                565                 570                 575
Ala Lys Lys Ala Ser Glu Ala Thr Met Tyr Val Thr Asp Lys Asp Asn
            580                 585                 590
Thr Ser Ser Lys Val His Leu Asn Asn Val Ser Asp Lys Phe Glu Val
            595                 600                 605
Thr Val Thr Val His Asn Lys Ser Asp Lys Pro His Glu Leu Tyr Tyr
610                 615                 620
Gln Ala Thr Val Gln Thr Asp Lys Val Asp Gly Lys His Phe Ala Leu
625                 630                 635                 640
Ala Pro Lys Ala Leu Ile Glu Thr Ser Trp Gln Lys Ile Thr Ile Pro
                645                 650                 655
Ala Asn Ser Ser Lys Gln Val Thr Ile Pro Ile Asp Ile Ser Gln Phe
            660                 665                 670
Ser Lys Asp Leu Leu Ala Gln Met Lys Asn Gly Tyr Phe Leu Glu Gly
            675                 680                 685
Phe Val Arg Ile Lys Gln Asp Pro Thr Lys Glu Glu Leu Met Ser Ile
690                 695                 700
Pro Tyr Ile Gly Phe Arg Gly Asp Phe Gly Asn Leu Ser Ala Leu Glu
705                 710                 715                 720
Lys Pro Leu Tyr Asp Ser Lys Asp Gly Ser Ser Tyr Tyr His Glu Glu
                725                 730                 735
Ile Ser Asp Ala Lys Asp Gln Leu Asp Gly Asp Gly Leu Gln Phe Tyr
            740                 745                 750
Ala Leu Lys Asn Asp Phe Thr Ala Leu Thr Thr Glu Ser Asn Pro Trp
            755                 760                 765
Thr Ile Ile Asn Val Val Lys Glu Gly Val Glu Asn Ile Glu Asp Ile
770                 775                 780
```

```
Glu Ser Ser Glu Ile Thr Glu Thr Ile Phe Ala Gly Thr Phe Ala Lys
785                 790                 795                 800

Gln Asp Asp Arg His Tyr Tyr Ile His Arg His Ala Asn Gly Lys
            805                 810                 815

Pro Tyr Ala Ala Ile Ser Pro Asn Gly Asp Gly Asn Arg Asp Tyr Val
            820                 825                 830

Gln Phe His Gly Thr Phe Leu Arg Asn Ala Lys Asn Leu Val Ala Glu
            835                 840                 845

Val Leu Asp Lys Glu Gly Asn Val Val Trp Thr Ser Glu Val Thr Glu
850                 855                 860

Gln Val Val Lys Asn Tyr Asn Asn Asp Leu Ala Ser Thr Leu Gly Ser
865                 870                 875                 880

Thr Arg Phe Glu Ile Ser Arg Trp Asp Gly Lys Asp Lys Asp Ala Lys
            885                 890                 895

Val Val Ala Asn Gly Thr Tyr Thr Tyr Arg Val Arg Tyr Thr Pro Ile
            900                 905                 910

Ser Ser Gly Ala Lys Glu Gln His Thr Asp Phe Asp Val Ile Val Asp
            915                 920                 925

Asn Thr Thr Pro Glu Val Ala Thr Ser Ala Thr Phe Ser Thr Glu Asp
930                 935                 940

Arg Arg Leu Thr Leu Ala Ser Lys Pro Gln Thr Ser Gln Pro Val Tyr
945                 950                 955                 960

Arg Glu Arg Ile Ala Tyr Thr Tyr Met Asp Glu Asp Leu Pro Thr Thr
            965                 970                 975

Glu Tyr Ile Ser Pro Asn Glu Asp Gly Thr Phe Thr Leu Pro Glu Glu
            980                 985                 990

Ala Glu Thr Met Glu Gly Ala Thr Val Pro Leu Lys Met Ser Asp Phe
            995                 1000                1005

Thr Tyr Val Val Glu Asp Met Ala Gly Asn Ile Thr Tyr Thr Pro Val
            1010                1015                1020

Thr Lys Leu Leu Glu Gly His Ser Asn Lys Pro Glu Gln Asp Gly Ser
1025                1030                1035                1040

Asp Gln Ala Pro Asp Lys Lys Pro Glu Thr Lys Pro Glu Gln Asp Gly
            1045                1050                1055

Ser Asp Gln Ala Pro Asp Lys Lys Pro Glu Thr Lys Pro Gly Gln Asp
            1060                1065                1070

Gly Ser Gly Gln Thr Pro Asp Lys Lys Pro Glu Thr Lys Pro Glu Lys
            1075                1080                1085

Asp Ser Ser Gly Gln Thr Pro Gly Lys Thr Pro Gln Lys Gly Gln Pro
            1090                1095                1100

Ser Arg Thr Leu Glu Lys Arg Ser Ser Lys Arg Ala Leu Ala Thr Lys
1105                1110                1115                1120

Ala Ser Thr Arg Asp Gln Leu Pro Thr Thr Asn Asp Lys Asp Thr Asn
            1125                1130                1135

Arg Leu His Leu Leu Lys Leu Val Met Thr Thr Phe Phe Leu Gly Leu
            1140                1145                1150

Val Ala His Ile Phe Lys Thr Lys Arg Thr Glu Asp
        1155                1160

<210> SEQ ID NO 2
<211> LENGTH: 1167
<212> TYPE: PRT
<213> ORGANISM: Streptococcus pyogenes
```

-continued

```
<400> SEQUENCE: 2

Leu Arg Lys Lys Gln Lys Leu Pro Phe Asp Lys Leu Ala Ile Ala Leu
 1               5                  10                  15

Met Ser Thr Ser Ile Leu Leu Asn Ala Gln Ser Asp Ile Lys Ala Asn
             20                  25                  30

Thr Val Thr Glu Asp Thr Pro Val Thr Glu Gln Ala Val Glu Thr Pro
         35                  40                  45

Gln Pro Thr Ala Val Ser Glu Val Pro Ser Ser Lys Glu Thr Lys
     50                  55                  60

Thr Pro Gln Thr Pro Asp Asp Ala Glu Glu Thr Ile Ala Asp Asp Ala
65                  70                  75                  80

Asn Asp Leu Ala Pro Gln Ala Pro Ala Lys Thr Ala Asp Thr Pro Ala
                 85                  90                  95

Thr Ser Lys Ala Thr Ile Arg Asp Leu Asn Asp Pro Ser Gln Val Lys
            100                 105                 110

Thr Leu Gln Glu Lys Ala Gly Lys Gly Ala Gly Thr Val Val Ala Val
            115                 120                 125

Ile Asp Ala Gly Phe Asp Lys Asn His Glu Ala Trp Arg Leu Thr Asp
130                 135                 140

Lys Thr Lys Ala Arg Tyr Gln Ser Lys Glu Asp Leu Glu Lys Ala Lys
145                 150                 155                 160

Lys Glu His Gly Ile Thr Tyr Gly Glu Trp Val Asn Asp Lys Val Ala
                165                 170                 175

Tyr Tyr His Asp Tyr Ser Lys Asp Gly Lys Thr Ala Val Asp Gln Glu
            180                 185                 190

His Gly Thr His Val Ser Gly Ile Leu Ser Gly Asn Ala Pro Ser Glu
            195                 200                 205

Thr Lys Glu Pro Tyr Arg Leu Glu Gly Ala Met Pro Glu Ala Gln Leu
210                 215                 220

Leu Leu Met Arg Val Glu Ile Val Asn Gly Leu Ala Asp Tyr Ala Arg
225                 230                 235                 240

Asn Tyr Ala Gln Ala Ile Arg Asp Ala Val Asn Leu Gly Ala Lys Val
                245                 250                 255

Ile Asn Met Ser Phe Gly Asn Ala Ala Leu Ala Tyr Ala Asn Leu Pro
            260                 265                 270

Asp Glu Thr Lys Lys Ala Phe Asp Tyr Ala Lys Ser Lys Gly Val Ser
            275                 280                 285

Ile Val Thr Ser Ala Gly Asn Asp Ser Ser Phe Gly Gly Lys Thr Arg
290                 295                 300

Leu Pro Leu Ala Asp His Pro Asp Tyr Gly Val Val Gly Thr Pro Ala
305                 310                 315                 320

Ala Ala Asp Ser Thr Leu Thr Val Ala Ser Tyr Ser Pro Asp Lys Gln
                325                 330                 335

Leu Thr Glu Thr Ala Met Val Lys Thr Asp Asp Gln Asp Lys Glu
            340                 345                 350

Met Pro Val Leu Ser Thr Asn Arg Phe Glu Pro Asn Lys Ala Tyr Asp
            355                 360                 365

Tyr Ala Tyr Ala Asn Arg Gly Met Lys Glu Asp Phe Lys Asp Val
370                 375                 380

Lys Gly Lys Ile Ala Leu Ile Glu Arg Gly Asp Ile Asp Phe Lys Asp
385                 390                 395                 400

Lys Val Ala Asn Ala Lys Lys Ala Gly Ala Val Gly Val Leu Ile Tyr
                405                 410                 415
```

```
Asp Asn Gln Asp Lys Gly Phe Pro Ile Glu Leu Pro Asn Val Asp Gln
            420                 425                 430

Met Pro Ala Ala Phe Ile Ser Arg Lys Asp Gly Leu Leu Leu Lys Asp
            435                 440                 445

Asn Pro Gln Lys Thr Ile Thr Phe Asn Ala Thr Pro Lys Val Leu Pro
            450                 455                 460

Thr Ala Ser Gly Thr Lys Leu Ser Arg Phe Ser Ser Trp Gly Leu Thr
465                 470                 475                 480

Ala Asp Gly Asn Ile Lys Pro Asp Ile Ala Ala Pro Gly Gln Asp Ile
                485                 490                 495

Leu Ser Ser Val Ala Asn Asn Lys Tyr Ala Lys Leu Ser Gly Thr Ser
            500                 505                 510

Met Ser Ala Pro Leu Val Ala Gly Ile Met Gly Leu Leu Gln Lys Gln
            515                 520                 525

Tyr Glu Thr Gln Tyr Pro Asp Met Thr Pro Ser Glu Arg Leu Asp Leu
            530                 535                 540

Ala Lys Lys Val Leu Met Ser Ala Thr Ala Leu Tyr Asp Glu Asp
545                 550                 555                 560

Glu Lys Ala Tyr Phe Ser Pro Arg Gln Gln Gly Ala Gly Ala Val Asp
                565                 570                 575

Ala Lys Lys Ala Ser Ala Ala Thr Met Tyr Val Thr Asp Lys Asp Asn
            580                 585                 590

Thr Ser Ser Lys Val His Leu Asn Asn Val Ser Asp Lys Phe Glu Val
            595                 600                 605

Thr Val Thr Val His Asn Lys Ser Asp Lys Pro Gln Glu Leu Tyr Tyr
610                 615                 620

Gln Ala Thr Val Gln Thr Asp Lys Val Asp Gly Lys His Phe Ala Leu
625                 630                 635                 640

Ala Pro Lys Val Leu Tyr Glu Ala Ser Trp Gln Lys Ile Thr Ile Pro
                645                 650                 655

Ala Asn Ser Ser Lys Gln Val Thr Val Pro Ile Asp Ala Ser Arg Phe
            660                 665                 670

Ser Lys Asp Leu Leu Ala Gln Met Lys Asn Gly Tyr Phe Leu Glu Gly
            675                 680                 685

Phe Val Arg Phe Lys Gln Asp Pro Thr Lys Glu Glu Leu Met Ser Ile
            690                 695                 700

Pro Tyr Ile Gly Phe Arg Gly Asp Phe Gly Asn Leu Ser Ala Val Glu
705                 710                 715                 720

Lys Pro Ile Tyr Asp Ser Lys Asp Gly Ser Ser Tyr Tyr His Glu Ala
                725                 730                 735

Asn Ser Asp Ala Lys Asp Gln Leu Asp Gly Asp Gly Leu Gln Phe Tyr
            740                 745                 750

Ala Leu Lys Asn Asn Phe Thr Ala Leu Thr Thr Glu Ser Asn Pro Trp
            755                 760                 765

Thr Ile Ile Lys Ala Val Lys Glu Gly Val Glu Asn Ile Glu Asp Ile
            770                 775                 780

Glu Ser Ser Glu Ile Thr Glu Thr Ile Phe Ala Gly Thr Phe Ala Lys
785                 790                 795                 800

Gln Asp Asp Asp Ser His Tyr Tyr Ile His Arg His Ala Asn Gly Glu
                805                 810                 815

Pro Tyr Ala Ala Ile Ser Pro Asn Gly Asp Gly Asn Arg Asp Tyr Val
            820                 825                 830
```

Gln Phe Gln Gly Thr Phe Leu Arg Asn Ala Lys Asn Leu Val Ala Glu
                835                 840                 845

Val Leu Asp Lys Glu Gly Asn Val Val Trp Thr Ser Glu Val Thr Glu
        850                 855                 860

Gln Val Val Lys Asn Tyr Asn Asp Leu Ala Ser Thr Leu Gly Ser
865                 870                 875                 880

Thr Arg Phe Glu Lys Thr Arg Trp Asp Gly Asp Lys Asp Gly Lys
                885                 890                 895

Val Val Ala Asn Gly Thr Tyr Thr Tyr Arg Val Arg Tyr Thr Pro Ile
                900                 905                 910

Ser Ser Gly Ala Lys Glu Gln His Thr Asp Phe Asp Val Ile Val Asp
            915                 920                 925

Asn Thr Thr Pro Glu Val Ala Thr Ser Ala Thr Phe Ser Thr Glu Asp
        930                 935                 940

Arg Arg Leu Thr Leu Ala Ser Lys Pro Lys Thr Ser Gln Pro Val Tyr
945                 950                 955                 960

Arg Glu Arg Ile Ala Tyr Thr Tyr Met Asp Glu Asp Leu Pro Thr Thr
                965                 970                 975

Glu Tyr Ile Ser Pro Asn Glu Asp Gly Thr Phe Thr Leu Pro Glu Glu
            980                 985                 990

Ala Glu Thr Met Glu Gly Ala Thr Val Pro Leu Lys Met Ser Asp Phe
        995                 1000                1005

Thr Tyr Val Val Glu Asp Met Ala Gly Asn Ile Thr Tyr Thr Pro Val
    1010                1015                1020

Thr Lys Leu Leu Glu Gly His Ser Asn Lys Pro Glu Gln Asp Gly Ser
1025                1030                1035                1040

Gly Gln Thr Pro Asp Lys Lys Pro Glu Ala Lys Pro Glu Gln Asp Gly
                1045                1050                1055

Ser Asp Gln Ala Pro Asp Lys Lys Pro Glu Ala Lys Pro Glu Gln Asp
        1060                1065                1070

Gly Ser Gly Gln Thr Pro Asp Lys Lys Pro Glu Thr Lys Pro Glu Lys
    1075                1080                1085

Asp Ser Ser Gly Gln Thr Pro Gly Lys Thr Pro Gln Lys Gly Gln Pro
1090                1095                1100

Ser Arg Thr Leu Glu Lys Arg Ser Ser Lys Ala Leu Ala Thr Lys
1105                1110                1115                1120

Ala Ser Thr Arg Asp Gln Leu Pro Thr Thr Asn Asp Lys Asp Thr Asn
                1125                1130                1135

Arg Leu His Leu Leu Lys Leu Val Met Thr Thr Phe Phe Gly Leu
                1140                1145                1150

Val Ala His Ile Phe Lys Thr Lys Arg Gln Lys Glu Thr Lys Lys
            1155                1160                1165

<210> SEQ ID NO 3
<211> LENGTH: 1150
<212> TYPE: PRT
<213> ORGANISM: Streptococcus agalactiae

<400> SEQUENCE: 3

Leu Arg Lys Lys Gln Lys Leu Pro Phe Asp Lys Leu Ala Ile Ala Leu
1               5                   10                  15

Met Ser Thr Ser Ile Leu Leu Asn Ala Gln Ser Asp Ile Lys Ala Asn
                20                  25                  30

Thr Val Thr Glu Asp Thr Pro Ala Thr Glu Gln Thr Val Glu Thr Pro
            35                  40                  45

```
Gln Pro Thr Ala Val Ser Glu Glu Ala Pro Ser Ser Lys Glu Thr Lys
    50                  55                  60

Thr Pro Gln Thr Pro Ser Asp Ala Gly Glu Thr Val Ala Asp Asp Ala
65                  70                  75                  80

Asn Asp Leu Ala Pro Gln Ala Pro Ala Lys Thr Ala Asp Thr Pro Ala
                85                  90                  95

Thr Ser Lys Ala Thr Ile Arg Asp Leu Asn Asp Pro Ser Gln Val Lys
            100                 105                 110

Thr Leu Gln Glu Lys Ala Gly Lys Gly Ala Gly Thr Val Val Ala Val
            115                 120                 125

Ile Asp Ala Gly Phe Asp Lys Asn His Glu Ala Trp Arg Leu Thr Asp
    130                 135                 140

Lys Thr Lys Ala Arg Tyr Gln Ser Lys Glu Asp Leu Glu Lys Ala Lys
145                 150                 155                 160

Lys Glu His Gly Ile Thr Tyr Gly Glu Trp Val Asn Asp Lys Val Ala
                165                 170                 175

Tyr Tyr His Asp Tyr Ser Lys Asp Gly Lys Thr Ala Val Asp Gln Glu
            180                 185                 190

His Gly Thr His Val Ser Gly Ile Leu Ser Gly Asn Ala Pro Ser Glu
            195                 200                 205

Thr Lys Glu Pro Tyr Arg Leu Glu Gly Ala Met Pro Glu Ala Gln Leu
    210                 215                 220

Leu Leu Met Arg Val Glu Ile Val Asn Gly Leu Ala Asp Tyr Ala Arg
225                 230                 235                 240

Asn Tyr Ala Gln Ala Ile Arg Asp Ala Ile Asn Leu Gly Ala Lys Val
                245                 250                 255

Ile Asn Met Ser Phe Gly Asn Ala Ala Leu Ala Tyr Ala Asn Leu Pro
            260                 265                 270

Asp Glu Thr Lys Lys Ala Phe Asp Tyr Ala Lys Ser Lys Gly Val Ser
        275                 280                 285

Ile Val Thr Ser Ala Gly Asn Asp Ser Ser Phe Gly Gly Lys Thr Arg
    290                 295                 300

Leu Pro Leu Ala Asp His Pro Asp Tyr Gly Val Val Gly Thr Pro Ala
305                 310                 315                 320

Ala Ala Asp Ser Thr Leu Thr Val Ala Ser Tyr Ser Pro Asp Lys Gln
                325                 330                 335

Leu Thr Glu Thr Val Arg Val Lys Thr Ala Asp Gln Gln Asp Lys Glu
            340                 345                 350

Met Pro Val Leu Ser Thr Asn Arg Phe Glu Pro Asn Lys Ala Tyr Asp
        355                 360                 365

Tyr Ala Tyr Ala Asn Arg Gly Thr Lys Glu Asp Asp Phe Lys Asp Val
    370                 375                 380

Lys Gly Lys Ile Ala Leu Ile Glu Arg Gly Asp Ile Asp Phe Lys Asp
385                 390                 395                 400

Lys Ile Ala Lys Ala Lys Lys Ala Gly Ala Val Gly Val Leu Ile Tyr
                405                 410                 415

Asp Asn Gln Asp Lys Gly Phe Pro Ile Glu Leu Pro Asn Val Asp Gln
            420                 425                 430

Met Pro Ala Ala Phe Ile Ser Arg Lys Asp Gly Leu Leu Leu Lys Asp
        435                 440                 445

Asn Pro Gln Lys Thr Ile Thr Phe Asn Ala Thr Pro Lys Val Leu Pro
    450                 455                 460
```

-continued

```
Thr Ala Ser Gly Thr Lys Leu Ser Arg Phe Ser Ser Trp Gly Leu Thr
465                 470                 475                 480

Ala Asp Gly Asn Ile Lys Pro Asp Ile Ala Ala Pro Gly Gln Asp Ile
            485                 490                 495

Leu Ser Ser Val Ala Asn Asn Lys Tyr Ala Lys Leu Ser Gly Thr Ser
                500                 505                 510

Met Ser Ala Pro Leu Val Ala Gly Ile Met Gly Leu Leu Gln Lys Gln
        515                 520                 525

Tyr Glu Thr Gln Tyr Pro Asp Met Thr Pro Ser Glu Arg Leu Asp Leu
530                 535                 540

Ala Lys Lys Val Leu Met Ser Ser Ala Thr Ala Leu Tyr Asp Glu Asp
545                 550                 555                 560

Glu Lys Ala Tyr Phe Ser Pro Arg Gln Gln Gly Ala Gly Ala Val Asp
                565                 570                 575

Ala Lys Lys Ala Ser Ala Ala Thr Met Tyr Val Thr Asp Lys Asp Asn
            580                 585                 590

Thr Ser Ser Lys Val His Leu Asn Asn Val Ser Asp Lys Phe Glu Val
        595                 600                 605

Thr Val Asn Val His Asn Lys Ser Asp Lys Pro Gln Glu Leu Tyr Tyr
610                 615                 620

Gln Ala Thr Val Gln Thr Asp Lys Val Asp Gly Lys His Phe Ala Leu
625                 630                 635                 640

Ala Pro Lys Val Leu Tyr Glu Ala Ser Trp Gln Lys Ile Thr Ile Pro
                645                 650                 655

Ala Asn Ser Ser Lys Gln Val Thr Val Pro Ile Asp Ala Ser Arg Phe
            660                 665                 670

Ser Lys Asp Leu Leu Ala Gln Met Lys Asn Gly Tyr Phe Leu Glu Gly
        675                 680                 685

Phe Val Arg Phe Lys Gln Asp Pro Lys Lys Glu Glu Leu Met Ser Ile
690                 695                 700

Pro Tyr Ile Gly Phe Arg Gly Asp Phe Gly Asn Leu Ser Ala Leu Glu
705                 710                 715                 720

Lys Pro Ile Tyr Asp Ser Lys Asp Gly Ser Ser Tyr Tyr His Glu Ala
                725                 730                 735

Asn Ser Asp Ala Lys Asp Gln Leu Asp Gly Asp Gly Leu Gln Phe Tyr
            740                 745                 750

Ala Leu Lys Asn Asn Phe Thr Ala Leu Thr Thr Glu Ser Asn Pro Trp
        755                 760                 765

Thr Ile Ile Lys Ala Val Lys Glu Gly Val Glu Asn Ile Glu Asp Ile
770                 775                 780

Glu Ser Ser Glu Ile Thr Glu Thr Ile Leu Ala Gly Thr Phe Ala Lys
785                 790                 795                 800

Gln Asp Asp Asp Ser His Tyr Tyr Ile His Arg His Ala Asn Gly Lys
                805                 810                 815

Pro Tyr Ala Ala Ile Ser Pro Asn Gly Asp Gly Asn Arg Asp Tyr Val
            820                 825                 830

Gln Phe Gln Gly Thr Phe Leu Arg Asn Ala Lys Asn Leu Val Ala Glu
        835                 840                 845

Val Leu Asp Lys Glu Gly Asn Val Val Trp Thr Ser Glu Val Thr Glu
850                 855                 860

Gln Val Val Lys Asn Tyr Asn Asn Asp Leu Ala Ser Thr Leu Gly Ser
865                 870                 875                 880

Thr Arg Phe Glu Lys Thr Arg Trp Asp Gly Lys Asp Lys Asp Gly Lys
```

```
                    885                 890                 895
Val Val Ala Asn Gly Thr Tyr Thr Tyr Arg Val Arg Tyr Thr Pro Ile
                900                 905                 910

Ser Ser Gly Ala Lys Glu Gln His Thr Asp Phe Asp Val Ile Val Asp
            915                 920                 925

Asn Thr Thr Pro Glu Val Ala Thr Ser Ala Thr Phe Ser Thr Glu Asp
        930                 935                 940

Arg Arg Leu Thr Leu Ala Ser Lys Pro Lys Thr Ser Gln Pro Val Tyr
945                 950                 955                 960

Arg Glu Arg Ile Ala Tyr Thr Tyr Met Asp Glu Asp Leu Pro Thr Thr
                965                 970                 975

Glu Tyr Ile Ser Pro Asn Glu Asp Gly Thr Phe Thr Leu Pro Glu Glu
            980                 985                 990

Ala Glu Thr Thr Glu Gly Ala Thr Val Pro Leu Lys Met Ser Asp Phe
        995                 1000                1005

Thr Tyr Val Val Glu Asp Met Ala Gly Asn Ile Thr Tyr Thr Pro Val
    1010                1015                1020

Thr Lys Leu Leu Glu Gly His Ser Asn Lys Pro Glu Gln Asp Gly Ser
1025                1030                1035                1040

Asp Gln Ala Pro Asp Lys Lys Pro Glu Ala Lys Pro Glu Gln Asp Gly
                1045                1050                1055

Ser Gly Gln Thr Pro Asp Lys Lys Thr Glu Thr Lys Pro Glu Lys Asp
            1060                1065                1070

Ser Ser Gly Gln Thr Pro Gly Lys Thr Pro Gln Lys Gly Gln Pro Ser
        1075                1080                1085

Arg Thr Leu Glu Lys Arg Ser Ser Lys Arg Ala Leu Ala Thr Lys Ala
    1090                1095                1100

Ser Thr Arg Asp Gln Leu Pro Thr Thr Asn Asp Lys Asp Thr Asn Arg
1105                1110                1115                1120

Leu His Leu Leu Lys Leu Val Met Thr Thr Phe Phe Leu Gly Leu Val
                1125                1130                1135

Ala His Ile Phe Lys Thr Lys Arg Gln Lys Glu Thr Lys Lys
            1140                1145                1150

<210> SEQ ID NO 4
<211> LENGTH: 31
<212> TYPE: DNA
<213> ORGANISM: Streptococcus pyogenes

<400> SEQUENCE: 4
gggggggaat cgtagcggg tatcatggga c                              31

<210> SEQ ID NO 5
<211> LENGTH: 31
<212> TYPE: DNA
<213> ORGANISM: Streptococcus pyogenes

<400> SEQUENCE: 5
gggggggaat cgggtgctg caatatctgg c                              31

<210> SEQ ID NO 6
<211> LENGTH: 17
<212> TYPE: DNA
<213> ORGANISM: Streptococcus pyogenes

<400> SEQUENCE: 6
gtaaaacgac ggccagt                                             17
```

<210> SEQ ID NO 7
<211> LENGTH: 19
<212> TYPE: DNA
<213> ORGANISM: Streptococcus pyogenes

<400> SEQUENCE: 7
aaggacgaca cattgcgta                                               19

<210> SEQ ID NO 8
<211> LENGTH: 31
<212> TYPE: DNA
<213> ORGANISM: Streptococcus pyogenes

<400> SEQUENCE: 8 cccccggat ccaccaaaac cccacaaact c                                  31

<210> SEQ ID NO 9
<211> LENGTH: 18
<212> TYPE: DNA
<213> ORGANISM: Streptococcus pyogenes

<400> SEQUENCE: 9
gagtggccct ccaatagc                                                18

<210> SEQ ID NO 10
<211> LENGTH: 35
<212> TYPE: DNA
<213> ORGANISM: Streptococcus pyogenes

<400> SEQUENCE: 10 cccccggat ccaatactgt gacagaagac actcc                              35

<210> SEQ ID NO 11
<211> LENGTH: 25
<212> TYPE: DNA
<213> ORGANISM: Streptococcus pyogenes

<400> SEQUENCE: 11
tttctggaac tagtatgtct gcgcc                                        25

<210> SEQ ID NO 12
<211> LENGTH: 41
<212> TYPE: DNA
<213> ORGANISM: Streptococcus pyogenes

<400> SEQUENCE: 12
ccccccctcg agatgtaaac gatttgtatc cttgtcatta g                      41

<210> SEQ ID NO 13
<211> LENGTH: 25
<212> TYPE: DNA
<213> ORGANISM: Streptococcus pyogenes

<400> SEQUENCE: 13
cagtgattga tgctggtttt gataa                                        25

<210> SEQ ID NO 14
<211> LENGTH: 18
<212> TYPE: DNA
<213> ORGANISM: Streptococcus pyogenes

<400> SEQUENCE: 14

-continued agctactatc agcaccag        18

<210> SEQ ID NO 15
<211> LENGTH: 38
<212> TYPE: DNA
<213> ORGANISM: Streptococcus pyogenes

<400> SEQUENCE: 15 cccccccgaat tcattactgt gacagaagac actcctgc        38

<210> SEQ ID NO 16
<211> LENGTH: 39
<212> TYPE: DNA
<213> ORGANISM: Streptococcus pyogenes

<400> SEQUENCE: 16
ccccccggat ccttattgtt ctggtttatt agagtggcc        39

<210> SEQ ID NO 17
<211> LENGTH: 33
<212> TYPE: DNA
<213> ORGANISM: Streptococcus pyogenes

<400> SEQUENCE: 17
attgctgctg gttttgataa aaatcatgaa gcg        33

<210> SEQ ID NO 18
<211> LENGTH: 18
<212> TYPE: DNA
<213> ORGANISM: Streptococcus pyogenes

<400> SEQUENCE: 18
cactgcaaca acagtccc        18

<210> SEQ ID NO 19
<211> LENGTH: 18
<212> TYPE: DNA
<213> ORGANISM: Streptococcus pyogenes

<400> SEQUENCE: 19
gaggccggca cacgtg        18

<210> SEQ ID NO 20
<211> LENGTH: 21
<212> TYPE: DNA
<213> ORGANISM: Streptococcus pyogenes

<400> SEQUENCE: 20
ttgatcgaca gcggttttac c        21

<210> SEQ ID NO 21
<211> LENGTH: 22
<212> TYPE: DNA
<213> ORGANISM: Streptococcus pyogenes

<400> SEQUENCE: 21
actgctatgt ctgctccatt ag        22

<210> SEQ ID NO 22
<211> LENGTH: 31
<212> TYPE: DNA
<213> ORGANISM: Streptococcus pyogenes

<400> SEQUENCE: 22
tccagaaagt ttggcatact tgttgttagc c    31

<210> SEQ ID NO 23
<211> LENGTH: 1181
<212> TYPE: PRT
<213> ORGANISM: Streptococcus pyogenes

<400> SEQUENCE: 23

```
Leu Arg Lys Lys Gln Lys Leu Pro Phe Asp Lys Leu Ala Ile Ala Leu
 1               5                  10                  15

Met Ser Thr Ser Ile Leu Leu Asn Ala Gln Ser Asp Ile Lys Ala Asn
            20                  25                  30

Thr Val Thr Glu Asp Thr Pro Ala Thr Glu Gln Ala Val Glu Thr Pro
        35                  40                  45

Gln Pro Thr Ala Val Ser Glu Glu Ala Pro Ser Ser Lys Glu Thr Lys
    50                  55                  60

Thr Pro Gln Thr Pro Asp Asp Ala Glu Glu Thr Ile Ala Asp Asp Ala
65                  70                  75                  80

Asn Asp Leu Ala Pro Gln Ala Pro Ala Lys Thr Ala Asp Thr Pro Ala
                85                  90                  95

Thr Ser Lys Ala Thr Ile Arg Asp Leu Asn Asp Pro Ser Gln Val Lys
            100                 105                 110

Thr Leu Gln Glu Lys Ala Gly Lys Gly Ala Gly Thr Val Val Ala Val
        115                 120                 125

Ile Asp Ala Gly Phe Asp Lys Asn His Glu Ala Trp Arg Leu Thr Asp
    130                 135                 140

Lys Thr Lys Ala Arg Tyr Gln Ser Lys Glu Asp Leu Glu Lys Ala Lys
145                 150                 155                 160

Lys Glu His Gly Ile Thr Tyr Gly Glu Trp Val Asn Asp Lys Val Ala
                165                 170                 175

Tyr Tyr His Asp Tyr Ser Lys Asp Gly Lys Thr Ala Val Asp Gln Glu
            180                 185                 190

His Gly Thr His Val Ser Gly Ile Leu Ser Gly Asn Ala Pro Ser Glu
        195                 200                 205

Thr Lys Glu Pro Tyr Arg Leu Glu Gly Ala Met Pro Glu Ala Gln Leu
    210                 215                 220

Leu Leu Met Arg Val Glu Ile Val Asn Gly Leu Ala Asp Tyr Ala Arg
225                 230                 235                 240

Asn Tyr Ala Gln Ala Ile Ile Asp Ala Val Asn Leu Gly Ala Lys Val
                245                 250                 255

Ile Asn Met Ser Phe Gly Asn Ala Ala Leu Ala Tyr Ala Asn Leu Pro
            260                 265                 270

Asp Glu Thr Lys Lys Ala Phe Asp Tyr Ala Lys Ser Lys Gly Val Ser
        275                 280                 285

Ile Val Thr Ser Ala Gly Asn Asp Ser Ser Phe Gly Gly Lys Thr Arg
    290                 295                 300

Leu Pro Leu Ala Asp His Pro Asp Tyr Gly Val Gly Thr Pro Ala
305                 310                 315                 320

Ala Ala Asp Ser Thr Leu Thr Val Ala Ser Tyr Ser Pro Asp Lys Gln
                325                 330                 335

Leu Thr Glu Thr Ala Thr Val Lys Thr Ala Asp Gln Asp Lys Glu
        340                 345                 350

Met Pro Val Leu Ser Thr Asn Arg Phe Glu Pro Asn Lys Ala Tyr Asp
    355                 360                 365
```

```
Tyr Ala Tyr Ala Asn Arg Gly Met Lys Glu Asp Phe Lys Asp Val
    370             375             380
Lys Gly Lys Ile Ala Leu Ile Glu Arg Gly Asp Ile Asp Phe Lys Asp
385             390             395             400
Lys Ile Ala Asn Ala Lys Lys Ala Gly Ala Val Gly Val Leu Ile Tyr
                405             410             415
Asp Asn Gln Asp Lys Gly Phe Pro Ile Glu Leu Pro Asn Val Asp Gln
            420             425             430
Met Pro Ala Ala Phe Ile Ser Arg Lys Asp Gly Leu Leu Leu Lys Glu
        435             440             445
Asn Pro Gln Lys Thr Ile Thr Phe Asn Ala Thr Pro Lys Val Leu Pro
450             455             460
Thr Ala Ser Gly Thr Lys Leu Ser Arg Phe Ser Ser Trp Gly Leu Thr
465             470             475             480
Ala Asp Gly Asn Ile Lys Pro Asp Ile Ala Ala Pro Gly Gln Asp Ile
                485             490             495
Leu Ser Ser Val Ala Asn Asn Lys Tyr Ala Lys Leu Ser Gly Thr Ser
            500             505             510
Met Ser Ala Pro Leu Val Ala Gly Ile Met Gly Leu Leu Gln Lys Gln
        515             520             525
Tyr Glu Thr Gln Tyr Pro Asp Met Thr Pro Ser Glu Arg Leu Asp Leu
    530             535             540
Ala Lys Lys Val Leu Met Ser Ser Ala Thr Ala Leu Tyr Asp Glu Asp
545             550             555             560
Glu Lys Ala Tyr Phe Ser Pro Arg Gln Gln Gly Ala Gly Ala Val Asp
                565             570             575
Ala Lys Lys Ala Ser Ala Ala Thr Met Tyr Val Thr Asp Lys Asp Asn
            580             585             590
Thr Ser Ser Lys Val His Leu Asn Asn Val Ser Asp Lys Phe Glu Val
        595             600             605
Thr Val Thr Val His Asn Lys Ser Asp Lys Pro Gln Glu Leu Tyr Tyr
    610             615             620
Gln Ala Thr Val Gln Thr Asp Lys Val Asp Gly Lys Leu Phe Ala Leu
625             630             635             640
Ala Pro Lys Ala Leu Tyr Glu Ala Ser Trp Gln Lys Ile Thr Ile Pro
                645             650             655
Ala Asn Ser Ser Lys Gln Val Thr Ile Pro Ile Asp Val Ser Gln Phe
            660             665             670
Ser Lys Asp Leu Leu Ala Pro Met Lys Asn Gly Tyr Phe Leu Glu Gly
        675             680             685
Phe Val Arg Phe Lys Gln Asp Pro Thr Lys Glu Glu Leu Met Ser Ile
    690             695             700
Pro Tyr Ile Gly Phe Arg Gly Asp Phe Gly Asn Leu Ser Ala Leu Glu
705             710             715             720
Lys Pro Ile Tyr Asp Ser Lys Asp Gly Ser Ser Tyr Tyr His Glu Ala
                725             730             735
Asn Ser Asp Ala Lys Asp Gln Leu Asp Gly Asp Gly Leu Gln Phe Tyr
            740             745             750
Ala Leu Lys Asn Asn Phe Thr Ala Leu Thr Thr Glu Ser Asn Pro Trp
        755             760             765
Thr Ile Ile Lys Ala Val Lys Glu Gly Val Glu Asn Ile Glu Asp Ile
    770             775             780
```

-continued

```
Glu Ser Ser Glu Ile Thr Glu Thr Ile Phe Ala Gly Thr Phe Ala Lys
785                 790                 795                 800

Gln Asp Asp Ser His Tyr Tyr Ile His Arg His Ala Asn Gly Lys
            805                 810                 815

Pro Tyr Ala Ala Ile Ser Pro Asn Gly Asp Gly Asn Arg Asp Tyr Val
                820                 825                 830

Gln Phe Gln Gly Thr Phe Leu Arg Asn Ala Lys Asn Leu Val Ala Glu
            835                 840                 845

Val Leu Asp Lys Glu Gly Asn Val Val Trp Thr Ser Glu Val Thr Glu
850                 855                 860

Gln Val Val Lys Asn Tyr Asn Asn Asp Leu Ala Ser Thr Leu Gly Ser
865                 870                 875                 880

Thr Arg Phe Glu Lys Thr Arg Trp Asp Gly Lys Asp Lys Asp Gly Lys
            885                 890                 895

Val Val Ala Asn Gly Thr Tyr Thr Tyr Arg Val Arg Tyr Thr Pro Ile
                900                 905                 910

Ser Ser Gly Ala Lys Glu Gln His Thr Asp Phe Asp Val Ile Val Asp
            915                 920                 925

Asn Thr Thr Pro Glu Val Ala Thr Ser Ala Thr Phe Ser Thr Glu Asp
930                 935                 940

Arg Arg Leu Thr Leu Ala Ser Lys Pro Lys Thr Ser Gln Pro Val Tyr
945                 950                 955                 960

Arg Glu Arg Ile Ala Tyr Thr Tyr Met Asp Glu Asp Leu Pro Thr Thr
            965                 970                 975

Glu Tyr Ile Ser Pro Asn Glu Asp Gly Thr Phe Thr Leu Pro Glu Glu
            980                 985                 990

Ala Glu Thr Met Glu Gly Ala Thr Val Pro Leu Lys Met Ser Asp Phe
            995                 1000                1005

Thr Tyr Val Val Glu Asp Met Ala Gly Asn Ile Thr Tyr Thr Pro Val
            1010                1015                1020

Thr Lys Leu Leu Glu Gly His Ser Asn Lys Pro Glu Gln Asp Gly Ser
1025                1030                1035                1040

Asp Gln Ala Pro Asp Lys Lys Pro Glu Thr Lys Pro Glu Gln Asp Gly
            1045                1050                1055

Ser Gly Gln Ala Pro Asp Lys Lys Pro Glu Thr Lys Pro Glu Gln Asp
            1060                1065                1070

Gly Ser Gly Gln Thr Pro Asp Lys Lys Pro Glu Thr Lys Pro Glu Gln
            1075                1080                1085

Asp Gly Ser Gly Gln Thr Pro Asp Lys Lys Pro Glu Thr Lys Pro Glu
            1090                1095                1100

Lys Asp Ser Ser Gly Gln Thr Pro Gly Lys Thr Pro Gln Lys Gly Gln
1105                1110                1115                1120

Pro Ser Arg Thr Leu Glu Lys Arg Ser Ser Lys Arg Ala Leu Ala Thr
            1125                1130                1135

Lys Ala Ser Thr Arg Asp Gln Leu Pro Thr Thr Asn Asp Lys Asp Thr
                1140                1145                1150

Asn Arg Leu His Leu Leu Lys Leu Val Met Thr Thr Phe Phe Leu Gly
            1155                1160                1165

Leu Val Ala His Ile Phe Lys Thr Lys Arg Thr Lys Lys
    1170                1175                1180
```

STREPTOCOCCAL C5A PEPTIDASE VACCINE

This application is a continuation-in-part of U.S. application Ser. No. 08/589,756 filed Jan. 22, 1996, now U.S. Pat. No. 5,846,547. U.S. Ser. No. 08/589,756 is incorporated by reference herein.

The invention was made with the support of NIH Grant No. AI 20016-11. The U.S. government has certain rights in the invention.

BACKGROUND OF THE INVENTION

There are several different β-hemolytic streptococcal species that have been identified. *Streptococcus pyogenes*, also called group A streptococci, is a common bacterial pathogen of humans. Primarily a disease of children, it causes a variety of infections including pharyngitis, impetigo and sepsis in humans. Subsequent to infection, autoimmune complications such as rheumatic fever and acute glomerulonephritis can occur in humans. This pathogen also causes severe acute diseases such as scarlet fever, necrotizing fasciitis and toxic shock.

Sore throat caused by group A streptococci, commonly called "strep throat," accounts for at least 16% of all office calls in a general medical practice, depending on the season. Hope-Simpson, E., "*Streptococcus pyogenes* in the throat: A study in a small population, 1962–1975," *J. Hyg. Camb.*, 87:109–129 (1981). This species is also the cause of the recent resurgence in North America and four other continents of toxic shock associated with necrotizing fasciitis. Stevens, D. L., "Invasive group A streptococcus infections," *Clin. Infect. Dis.*, 14:2–13 (1992). Also implicated in causing strep throat and occasionally in causing toxic shock are groups C and G streptococci. Hope-Simpson, E., "*Streptococcus pyogenes* in the throat: A study in a small population, 1962–1975," *J. Hyg. Camb.*, 87:109–129 (1981).

Group B streptococci, also known as *Streptococcus agalactiae*, are responsible for neonatal sepsis and meningitis. T. R. Maitin et al., "The effect of type-specific polysaccharide capsule on the clearance of group B streptococci from the lung of infant and adult rats", *J. Infect. Dis.*, 165:306–314 (1992). Although frequently a member of vaginal mucosal flora of adult females, from 0.1 to 0.5/1000 newborns develop serious disease following infection during delivery. In spite of the high mortality from group B streptococcal infections, mechanisms of the pathogenicity are poorly understood. Martin, T. R., et al., "The effect of type-specific polysaccharide capsule on the clearance of Group B streptococci from the lung of infant and adult rats," *J. Infect. Dis.*, 165:306–314 (1992).

Streptococcal infections are currently treated by antibiotic therapy. However, 25–30% of those treated have recurrent disease and/or shed the organism in mucosal secretions. At present no means is available to prevent streptococcal infections. Historically, streptococcal vaccine development has focused on the bacterium's cell surface M protein. Bessen, D., et al., "Influence of intranasal immunization with synthetic peptides corresponding to conserved epitopes of M protein on mucosal colonization by group A streptococci," *Infect. Immun.*, 56:2666–2672 (1988); Bronze, M. S., et al., "Protective immunity evoked by locally administered group A streptococcal vaccines in mice," *Journal of Immunology*, 141:2767–2770 (1988).

Two major problems will limit the use, marketing, and possibly FDA approval, of an M protein vaccine. First, more than 80 different M serotypes of *S. pyogenes* exist and new serotypes continually arise. Fischetti, V. A., "Streptococcal M protein: molecular design and biological behavior, *Clin. Microbiol. Rev.*, 2:285–314 (1989). Thus, inoculation with one serotype-specific M protein will not likely be effective in protecting against other M serotypes. The second problem relates to the safety of an M protein vaccine. Several regions of the M protein contain antigenic epitopes which are immunologically cross-reactive with human tissue, particularly heart tissue. The N-teimini of M proteins are highly variable in sequence and antigenic specificity. Inclusion of more than 80 different peptides, representing this variable sequence, in a vaccine would be required to achieve broad protection against group A streptococcal infection. New variant M proteins would still continue to arise, requiring ongoing surveillance of streptococcal disease and changes in the vaccine composition. In contrast, the carboxyl-termini of M proteins are conserved in sequence. This region of the M protein, however, contains an amino acid sequence which is immunologically cross-reactive with human heart tissue. This property of M protein is thought to account for heart valve damage associated with rheumatic fever. P. Fenderson et al., "Tropomyosinsharies immunologic epitopes with group A streptococcal M proteins, *J. Immunol.* 142:2475–2481 (1989). In an early trial, children who were vaccinated with M protein in 1979 had a ten fold higher incidence of rheumatic fever and associated heart valve damage. Massell, B. F., et al.," Rheumatic fever following streptococcal vaccination, *JAMA*, 207:1115–1119 (1969).

Other proteins under consideration for vaccine development are the erythrogenic toxins, streptococcal pyrogenic exotoxin A and streptococcal pyrogenic exotoxin B. Lee, P. K., et al., "Quantification and toxicity of group A streptococcal pyrogenic exotoxins in an animal model of toxic shock syndrome-like illness," *J. Clin. Microb.*, 27:1890–1892 (1989). Immunity to these proteins could prevent the deadly symptoms of toxic shock, but may not prevent colonization by streptococci.

Thus, there remains a continuing need for an effective means to prevent or ameliorate streptococcal infections. More specifically, a need exists to develop compositions useful in vaccines to prevent or ameliorate colonization of host tissues by streptococci, thereby reducing the incidence of strep throat and impetigo. Elimination of sequelae such as rheumatic fever, acute glomerulonephritis, sepsis, toxic shock and necrotizing fasciitis would be a direct consequence of reducing the incidence of acute infection and carriage of the organism. A need also exists to develop compositions useful in vaccines to prevent or ameliorate infections caused by all β-hemolytic streptococcal species, namely groups A, B, C and G.

SUMMARY OF THE INVENTION

The present invention provides a vaccine, and methods of vaccination, effective to immunize a susceptible mammal against β-hemolytic Streptococcus. The susceptible mammal could be a human or a domestic animal such as a dog, a cow, a pig or a horse. Such immunization could prevent, ameliorate or reduce the incidence of β-hemolytic Streptococcus colonization in the mammal. The vaccine contains an immunogenic amount of streptococcal C5a peptidase (SCP), wherein the SCP is a variant of wild-type SCP in combination with a physiologically-acceptable, non-toxic vehicle.

A "variant" of SCP is a polypeptide or oligopeptide SCP that is not completely identical to native SCP. Such a variant SCP can be obtained by altering the amino acid sequence by insertion, deletion or substitution of one or more amino acid.

The amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spacial conformation but has altered biological activity. For example, common conserved changes might be Asp to Glu, Asn or Gln; His to Lys, Arg or Phe; Asn to Gin, Asp or Gli and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparaginc and glutamine having uncharged polar side chains; aspartate and glutamate having acidic side chains; and lysine, arginine, and histidine having basic side chains. L. Stryer, *Biochemistry* (2d ed.) p. 14–15; Lehninger, *Biochemistry*, p. 73–75.

The amino acid changes are achieved by changing the codons of the corresponding nucleic acid sequence. It is known that such polypeptides can be obtained based on substituting certain amino acids for other amino acids in the polypeptide structure in order to modify or improve antigenic or immunogenic activity. For example, through substitution of alternative amino acids, small conformational changes may be conferred upon a polypeptide which result in increased activity or enhanced immune response. Alternatively, amino acid substitutions in certain polypeptides may be used to provide residues which may then be linked to other molecules to provide peptide-molecule conjugates which retain sufficient antigenic properties of the starting polypeptide to be useful for other purposes.

One can use the hydropathic index of amino acids in conferring interactive biological function on a polypeptide, wherein it is found that certain amino acids may be substituted for other amino acids having similar hydropathic indices and still retain a similar biological activity. Alternatively, substitution of like amino acids may be made on the basis of hydrophilicity, particularly where the biological function desired in the polypeptide to be generated in intended for use in immunological embodiments. The greatest local average hydrophilicity of a "protein", as governed by the hydrophilicity of its adjacent amino acids, correlates with its immunogenicity. U.S. Pat. No. 4,554,101. Accordingly, it is noted that substitutions can be made based on the hydrophilicity assigned to each amino acid.

In using either the hydrophilicity index or hydropathic index, which assigns values to each amino acid, it is preferred to conduct substitutions of amino acids where these values are ±2, with ±1 being particularly preferred, and those with in ±0.5 being the most preferred substitutions.

The variant SCP comprises at least seven amino acid residues, preferably about 100 to about 1500 residues, and more preferably about 300 to about 1200 residues, and even more preferably about 500 to about 1180 residues, wherein the variant SCP has at least 50%, preferably at least about 80%, and more preferably at least about 90% but less than 100%, contiguous amino acid sequence homology or identity to the amino acid sequence of a corresponding native SCP.

The amino acid sequence of the variant SCP polypeptide corresponds essentially to the native SCP amino acid sequence. As used herein "correspond essentially to" refers to a polypeptide sequence that will elicit a protective immunological response substantially the same as the response generated by native SCP. Such a response may be at least 60% of the level generated by native SCP, and may even be at least 80% of the level generated by native SCP. An immunological response to a composition or vaccine is the development in the host of a cellular and/or antibody-mediated immune response to the polypeptide or vaccine of interest. Usually, such a response consists of the subject producing antibodies, B cell, helper T cells, suppressor T cells, and/or cytotoxic T cells directed specifically to an antigen or antigens included in the composition or vaccine of interest.

The SCP may be a variant of SCP from group A Streptococcus (SCPA), group B Streptococcus (SCPB), group C Streptococcus (SCPC) or group G Streptococcus (SCPG).

A variant of the invention may include amino acid residues not present in the corresponding native SCP or deletions relative to the corresponding native SCP. A variant may also be a truncated "fragment" as compared to the corresponding native SCP, i.e., only a portion of a full-length protein. For example, the variant SCP may vary from native SCP in that it does not contain a cell wall insert. SCP variants also include peptides having at least one D-amino acid.

The variant SCP of the vaccine may be expressed from an isolated DNA sequence encoding the variant SCP. For example, the variant SCP may vary from native SCP in that it does not contain a signal sequence or a cell wall insert. The DNA may encode the specificity crevice or the catalytic domain. In particular the DNA may encode amino acid residue 130, 193, 295 or 512 of the catalytic domain, or amino acid residues 260, 261, 262, 415, 416 or 417 of the specificity crevice, or encode modifications at such residues. In particular, the DNA may encode SCPA49D130A, SCPA49H193A, SCPA49N295A, SCPA49S512A, SCPA1D130A, SCPA1H193A, SCPA1N295A, SCPA1S512A, SCPBD130A, SCPBH193A, SCPBN295A, SCPBS512A or ΔSCPA49. For the above listing SCPA49H193A means an SCP from group A Streptococci serotype 49, wherein the His at residue number 193 is replaced with Ala. The SCP of the vaccine may lack enzymatic C5ase or peptidase activity. The vaccine may also contain an immunological adjuvant. The vaccine can be used to prevent infection by group A Streptococcus, group B Streptococcus, group C Streptococcus or group G Streptococcus. The vaccine may comprise an immunogenic recombinant streptococcal C5a peptidase conjugated or linked to an immunogenic peptide or to an immunogenic polysaccharide. "Recombinant" is defined as a peptide or nucleic acid produced by the processes of genetic engineering. The terms "protein," "peptide" and "polypeptide" are used interchangeably herein.

The streptococcal C5a peptidase vaccine can be administered by subcutaneous or intramuscular injection. Alternatively, the vaccine can be administered by oral ingestion or intranasal inoculation.

The present invention further provides isolated and purified SCP peptides, wherein the SCP is a variant of wild-type SCP and isolated and purified polynucleotides encoding a variant SCP. For example, the SCP may include amino acid residue 130, 193, 295 or 512 of the catalytic domain, or amino acid residues 260, 261, 262, 415, 416 or 417 of the specificity crevice. The SCP may be SCPA49D130A, SCPA49H193A, SCPA49N295A, SCPA49S512A, SCPA1D130A, SCPA1H193A, SCPA1N295A, SCPA1S512A, SCPBD130A, SCPBH193A, SCPBN295A, SCPBS512A or ΔSCPA49.

BRIEF DESCRIPTION OF THE DRAWINGS

FIG. 2. Alignment of the amino acid sequence of SCP from group A streptococci serotype 49 (SEQ. ID. NO: 1), group A streptococci serotype 12 (SEQ. ID. NO: 2), group B streptococci (SEQ. ID. NO: 3) and group A streptococci serotype 1 (SEQ. ID. NO: 23). The sequences are identical except for the indicated amino acid positions. The triangle (∇) indicates the predicted cleavage point of the signal peptidase. Amino acids predicted to be in the enzyme's active site are marked by asterisks. Deletions in the amino acid sequence are indicated by dots and are boxed. The asterisks (*) indicate the amino acid residues of the catalytic domain.

FIG. 7. Construction of ΔSCPA49 vaccine and immunization protocol.

FIG. 9. Serum IgG and secretory IgA responses after intranasal immunization of mice with the purified ΔSCPA49 protein. Serum and saliva levels of SCPA49 specific IgG were determined by indirect ELISA. Sera from each mouse were diluted to 1:2,560 in PBS; saliva was diluted 1:2 in PBS.

FIG. 10. Comparison of the ability of serotype M49 streptococci to colonize immunized and non-immunized CD1 female mice. Each experimental group contained 13 mice which were infected intranasally (i.n.) with $2.0 \times 10^8$ CFU. The data were analyzed statistically by the $\chi^2$ test.

DETAILED DESCRIPTION OF THE INVENTION

Figure 1:
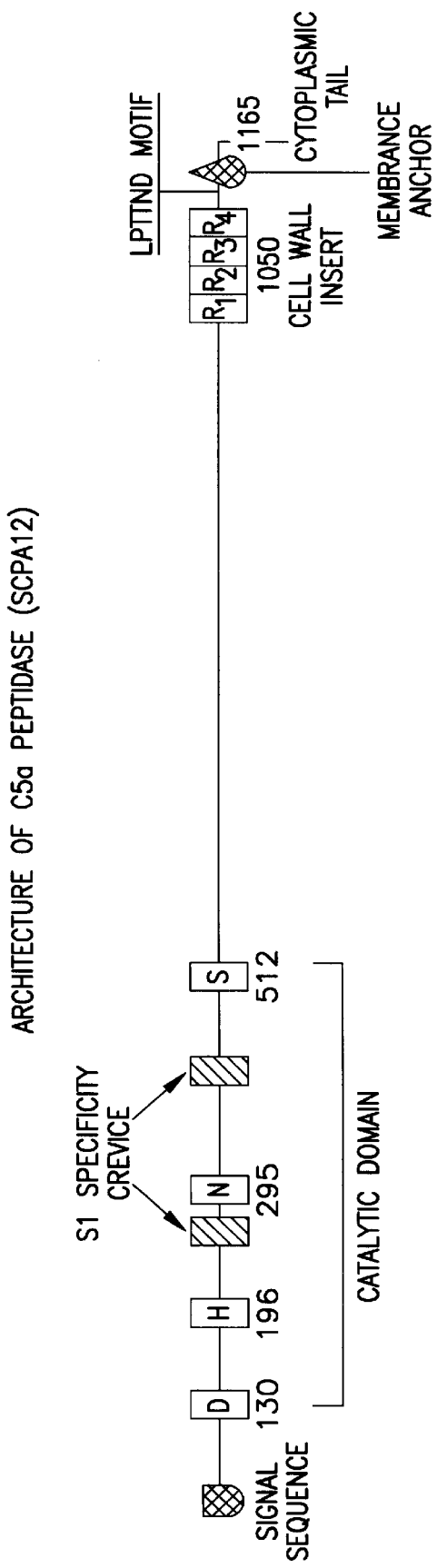
FIG. 1. Architecture of C5a peptidase from β-hemolytic streptococci. D indicates an aspartic acid residue; H indicates histidine; S indicates serine; L indicates leucine; P indicates proline; T indicates threonine; and N indicates asparagine. $R_1$, $R_2$, $R_3$ and $R_4$ indicate repeated sequences. The numbers indicate the amino acid residue position in the peptidase.

An important first line of defense against infection by many bacterial pathogens is the accumulation of phagocytic polymorphonuclear leukocytes (PMNs) and mononuclear cells at the site of infection. Attraction of these cells is mediated by chemotactic stimuli, such as host factors or factors secreted by the invading organism. The C5a chemoattractant is pivotal to the stimulation of this inflammatory response in mammals. C5a is a 74 residue glycopeptide cleaved from the fifth component (C5) of complement. Phagocytic cells respond in a directed manner to a gradient of C5a and accumulate at the site of infection. C5a may be the most immediate attractant of phagocytes during inflammation. As PMNs infiltrate an inflammatory lesion they secrete other chemokines, such as IL8, which further intensify the inflammatory response.

Streptococcal C5a peptidase (SCP) is a proteolytic enzyme located on the surface of pathogenic streptococci where it destroys C5a, as C5a is locally produced. SCP specifically cleaves the C5a chemotaxin at the PMN binding site (between $His^{67}$–$Lys^{68}$ residues of C5a) and removes the seven most C-terminal residues of C5a. This cleavage of the PMN binding site eliminates the chemotactic signal. Cleary, P., et al., "Streptococcal C5a peptidase is a highly specific endopeptidase," *Infect. Immun.*, 60:5219–5223 (1992); Wexler, D. E., et al., "Mechanism of action of the group A streptococcal C5a inactivator," *Proc. Natl. Acad. Sci. USA*, 82:8144–8148 (1985).

SCP from group A streptococci is a subtilisin-like serine protease with an $M_r$ of 124,814 da and with a cell wall anchor motif which is common to many Gram positive bacterial surface proteins. The architecture of C5a peptidase is given in FIG. 1. The complete nucleotides sequence of the streptococcal C5a peptidase gene of *Streptococcus pyogenes* has been published. Chen, C., and Cleary, P., "Complete nucleotide sequence of the streptococcal C5a peptidase gene of *Streptococcus pyogenes*," *J. Biol. Chem.*, 265:3161–3167 (1990). In contrast to Subtilisins, SCP has a very narrow substrate specificity. This narrow specificity is surprising in light of the marked similarities between their catalytic domains. Cleary, P., et al., "Streptococcal C5a peptidase is a highly specific endopeptide," *Infect. Immun.*, 60:5219–5223 (1992). Residues involved in charge transfer are conserved, as are residues on both sides of the binding pocket. However, the remaining amino acid sequence of SCP is unrelated to that of Subtilisins. More than 40 serotype of Group A streptococci were found to produce SCP protein or to harbor the gene. Cleary, P., et al., "A streptococcal inactivator of chemotaxis: a new virulence factor specific to group A streptococci," in *Recent Advances in Streptococci and Streptococcal Disease* p. 179–180 (S. Kotami and Y. Shiokawa ed.; Reedbooks Ltd., Berkshire, England; 1984); Podbielski, A., et al., "The group A streptococcal virR49 gene controls expression of four structural vir regulon genes," *Infect. Immun.*, 63:9–20 (1995).

The catalytic domain or active site of SCP is composed of the charge transfer system and the specificity crevice. The charge transfer system, also called the catalytic domain, contains residues $Asp^{130}$, $His^{193}$, $Asn^{295}$ and $Ser^{512}$ (FIGS. 1 and 2). A modification, i.e., a deletion, insertion or substitution, of any one of these amino acids will inactivate the enzyme. The specificity crevice, on the other hand, is predicted to be formed by $Ser^{260}$, $Phe^{261}$, $Gly^{262}$, $Ile^{415}$, $Tyr^{416}$ and $Asp^{417}$. Modification by substitution of these amino acids could change the substrate specificity of the enzyme or eliminate proteolytic activity altogether. Modification by deletion of these amino acids would also inactivate the enzyme. The catalytic domain depends on the tertiary structure of the protein that is created when the mature enzyme folds into its active state. This domain is not formed from a contiguous linear array of amino acid residues. Alternatively, modification may also reduce binding of variant SCP to the substrate. Binding may be reduced by 50%, 70% or even 80%.

A C5a peptidase enzyme associated with group B streptococci has also been identified. Hill, H. R., et al., "Group B streptococci inhibit the chemotactic activity of the fifth component of complement," *J. Immunol.* 141:3551–3556 (1988). Restriction mapping and completion of the scpB nucleotide sequence showed that scpB is 97–98% similar to scpA. See FIG. 2 for comparison of the amino acid sequence of SCP from group A streptococci serotype 49, group A streptococci serotype 12, group B streptococci and group A streptococci serotype 1 (SEQ. ID: 1, SEQ ID NO: 2, SEQ ID NO: 3 and SEQ ID NO: 23, respectively). More than 30 strains, representing all serotypes of group B streptococci carry the scpB gene. Cleary P. P., et al. "Similarity between the Group B and A streptococcal C5a Peptidase genes," *Infect. Immun.* 60:4239–4244 (1992); Suvorov A. N., et al., "C5a peptidase gene from group B streptococci," in *Genetics and Molecular Biology of Streptococci, Lactococci, and Enterococci* p. 230–232 (G. Dunny, P. Cleary and L. McKay (ed.); American Society for Microbiology, Washington, D.C.; 1991).

Human isolates of groups G and C streptococci also harbor scpA-like genes. Some group G strains were shown to express C5a specific protease activity on their surface. Cleary, P. P., et al., "Virulent human strains of group G streptococci express a C5a peptidase enzyme similar to that produced by group A streptococci," *Infect. Immun.*, 59:2305–2310 (1991). Therefore, all serotypes (>80) of group A streptococci, group B streptococci, group C streptococci and group G streptococci produce the SCP enzyme.

SCP assists streptococci to colonize a potential infection site, such as the nasopharyngeal mucosa, by inhibiting the influx of phagocytic white cells to the site of infection. This impedes the initial clearance of the streptococci by the host. The impact of SCP on inflammation, C5a leukocyte chemotaxis and streptococcal virulence was examined using streptococcal strains with well-defined mutations in the protease structural gene. SCP variants were constructed by targeted plasmid insertion and by replacement of the wild-type gene with scpA containing a specific internal deletion. Variants lacked C5a protease activity and did not inhibit the chemotactic response of human or mouse PMNs to C5a in vitro.

A mouse connective tissue air sac model was used to confirm that SCP retards the influx of phagocytic cells and clearance of streptococci from the site of infection. A connective tissue air sac is generated by injecting a small amount of air and PBS (with or without streptococci in it) with a 25-gauge needle under the skin on the back of a mouse. Boyle, M. D. P. et al., "Measurement of leukocyte chemotaxis in vivo," *Meth. Enzymol.*, 162:101:115 (1988). At the end of the experiment, the mice were euthanized by cervical dislocation, the air sacs dissected from the animals, and the air sacs homogenized in buffer. An advantage of the air sac model is that the air sac remains inflated for several days and free of inflammation, unless an irritant is injected. Thus, injected bacteria and the resulting inflammatory response remains localized over short periods of infection.

The air sac model was modified to compare clearance of wild-type $SCP^+$ and $SCP^-$ streptococci (i.e., group A streptococci which carried a variant non-functional form of SCP), and to analyze the cellular infiltrate at an early stage of infection. Tissue suspensions were assayed for viable streptococci on blood agar plates and the cellular infiltrate was analyzed by fluorescent cell sorting (FACS). In FACS analysis, individual cells in suspension are labelled with specific fluorescent monoantibodies. Aliquots of labelled cells are injected into a FAC-Scan flowcytometer, or fluorescent cell sorter, which counts cells based on their unique fluorescence. The experiments using the air sac model indicated that streptococci that were $SCP^+$ were more virulent than streptococci that were $SCP^-$.

A study was performed to measure production of human antibody, both IgG and IgA, against SCP in human sera and saliva. O'Connor, SP, et al., "The Human Antibody Response to Streptococcal C5a Peptidase," *J. Infect. Dis.* 163:109–16 (1991). Generally, sera and saliva from young, uninfected children lacked antibody to SCP. In contrast, most sera and saliva specimens from healthy adults had measurable levels of anti-SCP IgG and SCP-specific secretory IgA (anti-SCP sIgA). Paired acute and convalescent sera from patients with streptococcal pharyngitis possessed significantly higher levels of anti-SCP IgG than did sera from healthy individuals. Sera containing high concentrations of anti-SCP immunoglobulin were capable of neutralizing SCP activity. Detection of this antibody in >90% of the saliva specimens obtained from children who had recently experienced streptococcal pharyngitis demonstrated that children can produce an antibody response.

Even though the human subjects produced IgG and IgA against SCP in response to a natural streptococcal infection, it was not known whether the anti-SCP immunoglobulin provides any protection against infection. Further, it was not known if the SCP protein could act as a vaccine against β-hemolytic streptococcal colonization or infection. First, a study was performed to examine the role of SCP in colonization of the nasopharynx. Following intranasal infection with live group A streptococci, throat cultures were taken daily for up to ten days. Wild-type and isogenic SCP-deficient mutant streptococci were compared for the ability to persist in the throat over this ten day period. As predicted, the SCP-deficient mutant streptococci were cleared from the nasopharynx more rapidly.

The same intranasal mouse model was used to test the capacity of SCP to induce immunity that will prevent colonization. A variant form of the recombinant scpA49 gene beginning at the nucleotide that encodes Thr$^{63}$ was cloned. This variant is referred to as ΔSCPA49, and is 2908 bp in length (see Example 4 below). Variant SCP protein was purified from an *E. coli* recombinant by affinity chromatography. Sera from rabbits vaccinated intradermally with this protein preparation neutralized SCP activity in vitro. Purified protein (40 μg) was administered intranasally to mice over a period of five weeks. Immunized mice cleared streptococci in 1–2 days; whereas, throat cultures of non-immunized mice remained positive for up to 10 days. The experiment was repeated on three sets of mice, vaccinated with three separate preparations of a SCP protein.

Further experiments were performed to determine whether immunization of an animal with a single antigen would prevent colonization by several serotypes. ΔSCPA49 was cloned into an expression vector and expressed in *E. coli*. The affinity purified variant ΔSCPA49 protein proved to be highly immunogenic in mice and rabbits. Although the purified variant ΔSCPA49 immunogen lacked enzymatic activity, it induced high titers of rabbit antibodies that were able to neutralize peptidase activity associated with M1, M6, M12 and M49 streptococci in vitro. This confirmed that anti-peptidase antibodies lack serotype specificity. Four sets of mice were then intranasally immunized with the purified variant ΔSCPA49 and each was challenged with a different serotype of group A streptococcus. The immunization of mice with ΔSCPA49 protein stimulated significant levels of specific salivary sIgA and serum IgG antibodies and reduced the potential of wild-type M1, M2, M6, M11 and M49 streptococci to colonize. These experiments confirm that immunization with streptococcal C5a peptidase vaccine is effective in preventing the colonization of the nasopharynx.

Experiments were also performed to develop variant SCPs from an M1 OF$^-$ strain and from the M49 OF$^+$ strain. Since active SCP could be harmful to the host, it was important that the variant proteins lacked enzymatic activity. Amino acids that are required for catalytic activity were replaced with those expected to inactivate the enzyme.

Two properties of the variant proteins were evaluated. First, the specific activities of the wild-type and variant proteins were determined by PMN adherence assay. These experiments indicated that the substituted amino acids reduced enzymatic activity by greater than 90%. Second, the variant proteins were also compared to the wild-type protein for their capacity to bind antibody directed against the wild-type enzyme. Competitive ELISA assays were used for this purpose. The results indicated that the amino acid substitutions did not alter the ability of antibody to bind to the variant proteins.

All earlier protection studies had been performed by administering affinity purified ΔSCPA49 protein intranasally without adjuvant. Intramuscular or subcutaneous (SQ) injection of antigens, however, is historically a preferred, more accepted method of vaccine delivery. Therefore, experiments were performed to test whether SQ injections of ΔSCPA with monophosphoryl lipid A (MPL) and alum (Al PO$_4$) induced a protective immune response and whether that response reduced colonization when the challenge strain of group A streptococcus differed in serotype from the source of the SCPA vaccine. The capacity of immunized mice to clear streptococci from the oral-nasal pharyngeal mucosa was evaluated by throat culture or by sampling dissected nasal tissue.

The number of streptococci associated with nasal tissue decreased with time, as expected, and the decrease was more rapid and complete in mice immunized with SCPA antigen. The results confirmed that a single SCPA antigen can induce protection against heterologous serotypes. Protection is afforded by antibody that neutralizes peptidase activity on the bacterial surface. This increases the influx of phagocytes within a few hours from the time streptococci are deposited on mucosal tissue. Rapid clearance of streptococci by phagocytes is presumed to prevent subsequent multiplication and persistence of the bacteria. Thus, SQ injection of SCPA antigen with adjuvant consistently induced a vigorous antibody response.

The present invention thus provides a vaccine for use to protect mammals against β-hemolytic Streptococcus colonization or infection. In one embodiment of this invention, as is customary for vaccines, the variant streptococcal C5a peptidase can be delivered to a mammal in a pharmacologically acceptable vehicle. Vaccines of the present invention can also include effective amounts of immunological adjuvants, known to enhance an immune response.

The SCP can be conjugated or linked to another peptide or to a polysaccharide. For example, immunogenic proteins well-known in the art, also known as "carriers," may be employed. Useful immunogenic proteins include keyhole limpet hemocyanin (KLH), bovine serum albumin (BSA), ovalbumin, human serum albumin, human gamma globulin, chicken immunoglobulin G and bovine gamma globulin. Useful immunogenic polysaccharides include group A Streptococcal polysaccharide, C-polysaccharide from group B Streptococci, or the capsular polysaccharides of *Streptococcus pneumoniae* or group B Streptococci. Alternatively, polysaccharides or proteins of other pathogens that are used as vaccines can be conjugated to, linked to, or mixed with SCP.

Further provided are isolated and purified nucleic acid molecules, e.g., DNA molecules, comprising a preselected nucleic acid segment which encodes at least a portion of a Streptococcal C5a peptidase, i.e., they encode SCP or a variant thereof as described herein, e.g., SCPA49S512A, SCPA49D130A, SCPA49N295A, SCPA1S512A, SCPA1D130A, SCPA1N295A, ΔSCPA49, SCPBS512A, SCPBD130A, SCPBH193A or SCPBN295A, or any combination of these mutations. For example, the invention provides an expression cassette comprising a preselected DNA segment which codes for an RNA molecule which is substantially identical (sense) to all or a portion of a messenger RNA ("target" mRNA), i.e., an endogenous or "native" SCP mRNA. The preselected DNA segment in the expression cassette is operably linked to a promoter. As used herein, "substantially identical" in sequence means that two nucleic acid sequences have at least about 65%, preferably about 70%, more preferably about 90%, and even more preferably about 98%, contiguous nucleotide sequence identity to each other. Preferably, the preselected DNA segment hybridizes under hybridization conditions, preferably under stringent hybridization conditions, to a nucleic acid molecule encoding the corresponding native SCP.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

As used herein, the term "recombinant nucleic acid" or "preselected nucleic acid," e.g., "recombinant DNA sequence or segment" or "preselected DNA sequence or segment" refers to a nucleic acid, e.g., to DNA, that has been derived or isolated from any appropriate source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.*, 9, 6103 (1981), and Goeddel et al., *Nucleic Acids Res.*, 8, 4057 (1980). Therefore, "preselected DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular DNA molecule.

Nucleic acid molecules encoding amino acid sequence variants of a SCP are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the SCP.

To immunize a subject, the variant SCP, is administered parenterally, usually by intramuscular or subcutaneous injection in an appropriate vehicle. Other modes of administration, however, such as oral delivery or intranasal delivery, are also acceptable. Vaccine formulations will contain an effective amount of the active ingredient in a vehicle. The effective amount is sufficient to prevent, ameliorate or reduce the incidence of β-hemolytic Streptococcus colonization in the target mammal. The effective amount is readily determined by one skilled in the art. The active ingredient may typically range from about 1% to about 95% (w/w) of the composition, or even higher or lower if appropriate. The quantity to be administered depends upon factors such as the age, weight and physical condition of the animal or the human subject considered for vaccination. The quantity also depends upon the capacity of the animal's immune system to synthesize antibodies, and the degree of protection desired. Effective dosages can be readily established by one of ordinary skill in the art through routine trials establishing dose response curves. The subject is immunized by administration of the SCP in one or more doses. Multiple doses may be administered as is required to maintain a state of immunity to streptococci.

Intranasal formulations may include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Oral liquid preparations may be in the form of, for example, aqueous or oily suspension, solutions, emulsions, syrups or elixirs, or may be presented dry in tablet form or a product for reconstitution with water or other suitable vehicle before use. Such liquid preparations may contain conventional additives such as suspending agents, emulsifying agents, non-aqueous vehicles (which may include edible oils), or preservative.

To prepare a vaccine, the purified SCP can be isolated, lyophilized and stabilized. The SCP peptide may then be adjusted to an appropriate concentration, optionally combined with a suitable vaccine adjuvant, and packaged for use. Suitable adjuvants include but are not limited to surfactants, e.g., hexadecylamine, octadecylamine, lysolecithin, dimethyldioctadecylammonium bromide, N,N-dioctadecyl-N'-N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, MPL, aimethylglycine, tuftsin, oil emulsions, alum, and mixtures thereof. Other potential adjuvants include the B peptide subunits of *E. coli* heat labile toxin or of the cholera toxin. McGhee, J. R., et al., "On vaccine development," *Sem. Hematol.*, 30:3–15 (1993). Finally, the immunogenic product may be incorporated into liposomes for use in a vaccine formulation, or may be conjugated to proteins such as keyhole limpet hemocyanin (KLH) or human serum albumin (HSA) or other polymers.

The application of SCP for vaccination of a mammal against colonization offers advantages over other vaccine candidates. Prevention of colonization or infection by inoculation with a single protein will not only reduce the incidence of the very common problems of strep throat and impetigo, but will also eliminate sequelae such as rheumatic fever, acute glomerulonephritis, sepsis, toxic shock and necrotizing fasciitis.

The following examples are intended to illustrate but not limit the invention.

EXAMPLE 1

Construction and In Vitro Analysis of Insertion and Deletion Mutants in scpA49 and scpA6 a) Bacterial strains and culture conditions. *S. pyogenes* strain CS101 is a serotype M49, and scrim opacity positive (OF$^+$)strain. CS159 is a clinical isolate with a deletion which extends through the M gene cluster and scpA. A spontaneous, streptomycin resistant derivative of strain CS101, named CS101Sm, was selected by plating streptococci from a stationary phase culture on tryptose blood agar containing streptomycin (200 μg/ml). Streptococcal strains CS210 and CS463 are spontaneous streptomycin resistant derivatives of OF$^+$, class II, serotype M2, and M11 strains, respectively. Streptococcal strains 90–131 and UAB200 are spontaneous streptomycin resistant derivatives of OF$^-$, class I, serotype M1 and M6 human isolates of group A streptococci, respectively.

CS101::pG+host5 is strain CS101 with pG+host5 integrated into the chromosome at an unknown location, but outside scpA and the emm gene cluster. *Escherichia coli* strain ER1821 (from New England Biolabs, Inc. Beverly, Mass.) was used as the recipient for the suicide vector, plasmid pG+host5. Plasmid pG+host5 was obtained from Appligene, Inc. Pleasanton, Calif. Streptococci were grown in Todd-Hewitt broth supplemented with 2% neopeptone or 1% yeast extract, or on tryptose agar plates with 5% sheep blood. *E. coli* strain ER1821 containing plasmid pG+host5 was grown in LB broth with erythromycin (300 µg/ml). Streptococci with plasmid pG+host5 were cultured in Todd-Hewitt broth with 1% yeast extract (THY) containing 1 µg/ml of erythromycin (Erm).

Figure 3:
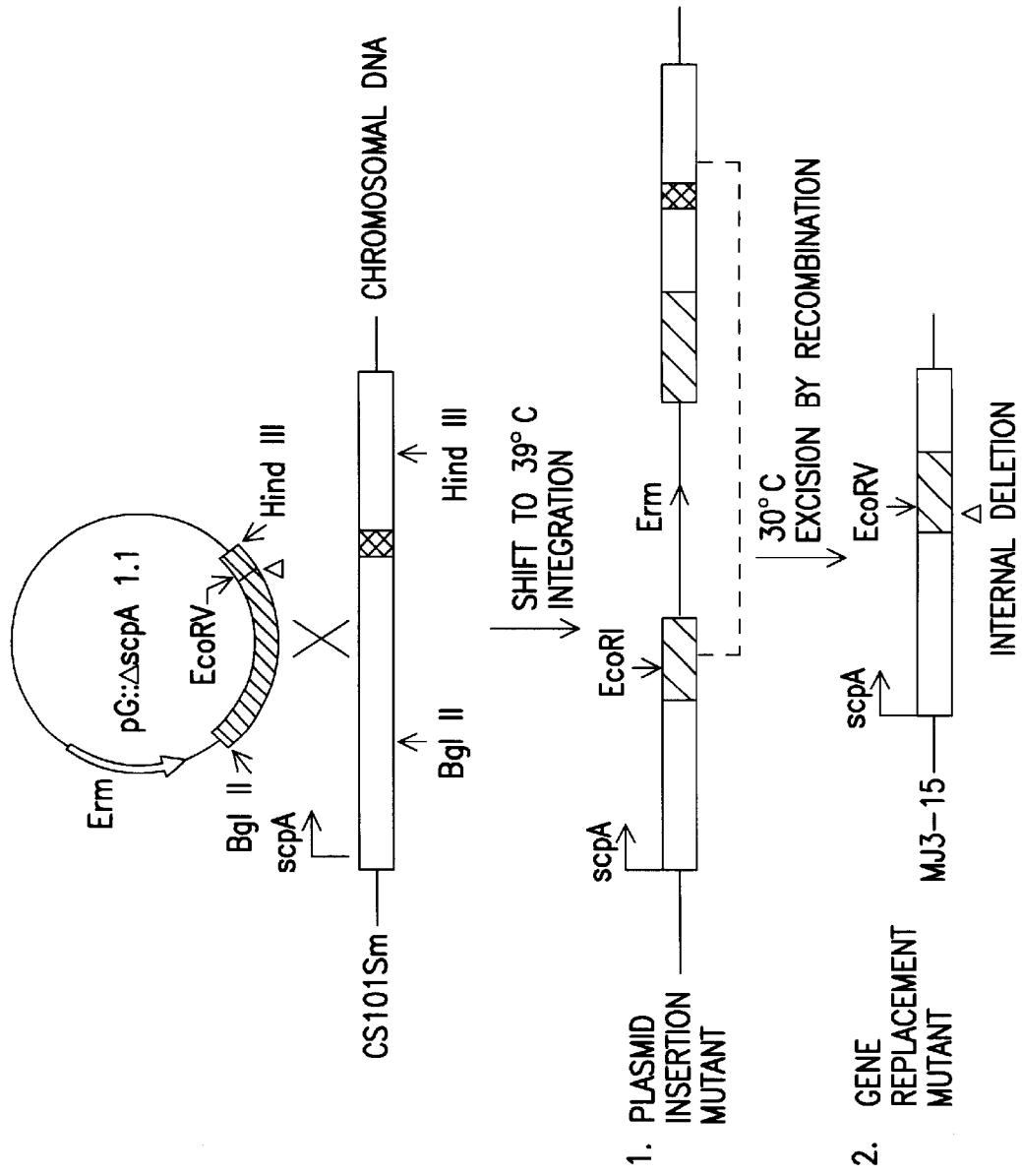
FIG. 3. Constriction of SCP insertion and deletion mutants. Black box indicates deleted region.

SCP refers to streptococcal C5a peptidase from β-hemolytic Streptococcus generally. SCPA1, SCPA12, SCPA49, SCPA6 are the specific peptidases from group A Streptococcus M serotype 1, 12, 49 and 6 strains, respectively. The term scpA refers to the gene encoding SCP from group A streptococci. ScpA1, scpA12, scpA6 and scpA49 are the genes encoding the SCPA1, SCPA12, SCPA49 and SCPA6 peptidases. SCPB and scpB refer to the peptidase and gene from group B streptococci. The amino acid sequences for SCPA49 (SEQ. ID. NO: 1), SCPA12 (SEQ. ID. NO: 2), SCPA1 (SEQ. ID. NO: 23) and SCPB (SEQ. ID. NO: 3) are given in FIG. 2.

b) Construction of scpA49 insertion mutant. Well-defined insertion mutants of scpA49 were constructed using plasmid insertion and gene replacement methods. An internal scpA49 BglII-BamHI fragment, the insertion target, was ligated into the thermosensitive shuttle vector pG+host5 to form plasmid pG::scpA1.2 and transformed into *E. coli* ER1821 (FIG. 3). The pG+host5 vector contains an *E. coli* origin of replication that is active at 39° C., a temperature sensitive Gram positive origin of replication (active at 30° C. and inactive at 39° C. in streptococci), and an erythromycin resistance gene for selection. High temperature forces the plasmid to integrate into the chromosomal DNA of group A streptococci by homologous recombinant at frequencies ranging from $10^{-2}$ to $10^{-3}$.

Recombinant plasmid DNA pG::scpA1.2 was electroporated into CS101 recipient cells. Transformants were selected on THY-agar plates containing 1 µg/ml erythromycin at 30° C. Chromosomal integrants which resulted from recombination between the plasmid insert and the chromosomal scpA49 were selected by erythromycin resistance at 39° C. Two insertion mutants, M14 and M16, were analyzed. EmrS revertants of strain M14 and M16 were obtained by passage in THY without antibiotic at 30° C. and finally plated at 37° C. without Ern selection. Colonies that had lost the plasmid were isolated to confirm that the mutant phenotype resulted from insertion of the plasmid into scpA49, rather than from a simultaneous unrelated mutation.

c) Construction of the scpA6 insertion mutants. The scpA6 insertion mutant AK1.4 was constructed as described in section (b) above. Recombinant plasmid DNA, pG::scpA1.2, contains an internal BglII-HindIII fragment of scpA gene. This plasmid was electroporated into UAB200 recipient cells and transformants were selected on THY agar plates containing erythromycin at 30° C. A chromosomal integrant of pG::scpA1.2, strain AK1.4, which resulted from recombination between the plasmid insert and the chromosomal scpA6 was selected by growth on agar medium containing erythromycin at 39° C. Insertion into scpA6 was confirmed by Southern blotting using scpA as the probe, and PCR using an M13 universal primer (5'-GTAAAACGACGGCCAGT-3') (SEQ. ID. NO: 6), specific for the plasmid, and an scpA For835 primer (5'-AAGGACGACACATTGCGTA-3') (SEQ. ID. NO: 7), specific for the chromosomal scpA of GAS.

d) Introduction of a defined deletion into scpA (FIG. 3). A mutant strain with a defined deletion internal to scpA49 was constructed to eliminate the possibility that insertions in scpA49 could be polar and reduce expression of downstream genes, unknown genes which could also contribute to the organism's virilence. First, a defined deletion in BglII-HindIII fragment of scpA was produced by inside-out PCR with primer 1 (5'-GGGGGGGAATTC GTAGCGGGTATCATGGGAC-3'), SEQ. ID. NO: 4, and primer 2 (5'-GGGGGGGAATTC GGGTGCTGCAATATCTGGC-3'), SEQ. ID. NO: 5. Underlined nuclcotides correspond to scpA sequences with coordinates 2398 and 2322, respectively, and the bold faced nucleotides correspond to a EcoRI recognition site. The primers were selected to produce an in-frame deletion in the scpA gene. These primers copy plasmid DNA in opposite directions and define the boundaries of the deletion. Innis, M. A., et al., eds., *PCR Protocols A Guide to Methods and Applications* (Academic Press, 1990). Plasmid pG::scpA1.2 DNA was used as template.

The amplified product was digested with EcoRI and ligated to plasmid pG+host5. The resulting plasmid pG::ΔscpA1.1 contained an 76 bp deletion internal o scpA. This in-frame deletion removed 25 amino acids, including the serine which forms part of the predicted catalytic center of serine proteases. Chen, C., and Cleary, P., "Complete nucleotide sequence of the streptococcal C5a peptidase gene of *Streptococcus pyogenes*," *J. Biol. Chem.*, 265:3161–3167 (1990). An EcoRV site was created at the point of deletion. DNA which overlaps the deletion was sequenced to confirm the boundaries of the deletion.

The plasmid pG::ΔscpA1.1, which contains the deletion, was transformed into *E. coli* ER1821. Colonies were selected for ErmR and then screened for the appropriate scpA deletion using miniprep plasmid DNA restricted by EcoRI. The precise boundaries of the deletion were confirmed by DNA sequencing. Plasmid pG::ΔscpA1.1 was electroporated into strain CS101Sm as described above, then integrants were selected by grown on Erm at 39° C. Integration of the plasmid into the chromosome of the M49 strain CS101sm using high temperature selection. The insertion location was confirmed by PCR. Growth of CS101Sm (pG::ΔscpA1.1) at low temperature without erythromycin selection resulted in high frequency segregation of ErmS revertants which have lost the plasmid by random deletion event or by excision due to recombination between the duplicated scpA sequences created by the insertion. Two deletion mutants were identified, MJ2-5 and MJ3-15, and were studied further. The chromosomal deletion left behind by recombinational excision of plasmid pG::ΔscpA1.1 was defined by PCR and Southern hybridization to EcoRV digested DNA.

e) In vitro effects of mutations on SCP. The impact of insertions and deletions on the expression of SCP antigen and peptidase activity was assessed by Western blot and PMNs adherence assays. Streptococci were incubated in 100 ml THY at 37° C. overnight. The culture pellet was washed two times in 5 ml cold 0.2 M NaAcetate (pH 5.2), then suspended in 1 ml TE-sucrose buffer (20% sucrose 10 mM Tris, 1 mM EDTA, pH 7.0) and 40 µl Mutanolysin. The mixture was rotated at 37° C. for 2 hr, then centrifuged 5 min at 4500 rpm. Supernatants contained protease inhibitor, 100 mM phenylmethyl sulfonyl fluoride (PMSF). Electrophoresis and Western blotting methods were performed as described in Laemmli, U. K., "Cleavage of structural proteins during the assembly of the head of bacteriophage T4," *Nature* 227:680–685 (1970). The primary antiserum used to detect SCP protein on Western and colony blots was prepared by immunization of a rabbit with purified recombinant SCP protein. Binding was detected by anti-rabbit antibody alkaline phosphatase conjugate.

C5a peptidase activity was measured using a PMN adherence assay. Booth, S. A. et al., "Dapsone suppresses integrin-mediated neutrophil adherence function," *J. Invest. Dermatol.* 98:135–140 (1992). After incubation of C5a (Sigma, St. Louis, Mo.) with streptococcal extracts or purified protease, residual C5a can activate PMNs to become adherent to BSA coated wells. First, microtiter wells were coated with 0.5% BSA in PBS and incubated for 1 hr at 37° C. Human PMNs were isolated by centrifugation in Ficoll Hypaque (Sigma, St. Louis, Mo.). 40 $\mu$l of intact streptococci or protein extracts were incubated with 20 $\mu$l of 5 $\mu$M C5a in 340 $\mu$l of PBS with 1% glucose and 0.1% $CaCl_2$ at 37° C. for 45 min. BSA-coated wells were washed with PBS, and resuspended PMNs and residual C5a were added to wells. The mixture was incubated for 45 min at 37° C. in 7% $CO_2$. Finally, wells were washed to remove nonadherent PMNs. Adherent PMNs were stained with crystal violet and the $OD_{570nm}$ was read in an ELISA reader. The optical density is proportional to the amount of residual C5a or inversely proportional to the amount of SCP activity.

Mutanolysin extracts of cell surface proteins from parent and mutant cultures were analyzed by Western blot using SCPA specific serum. Mutants were confirmed to lack SCPA. Extracts of SCPA$^-$ mutants AK1.4 and MJ3-15 did not react with anti-SCPA serum. SCPA proteins of the expected size were observed in extracts from the wild-type strains CS101 and UAB200. Failure of mutant strains AK1.4 and MJ3-15 to produce C5a peptidase activity was verified by comparing their capacity to destroy rhC5a. Exposure of isolated PMNs to rhC5a induced them to become adherent to BSA coated microtiter wells. Incubation with streptococci or purified SCPA specifically cleaved rhC5a and altered its potential to activate PMNs. PMNs that responded to residual rhC5a and bound to BSA coated wells, were stained, then measured spectrophotometrically. Incubation of rhC5a with parent cultures UAB200 and CS101 destroyed rhC5a, which inhibited PMN adherence by 58.8% and 54.5%, respectively. In contrast SCPA$^-$ mutants, AK1.4 and MJ3-15, did not alter rhC5a or adherence of PMNs to BSA coated wells (Table 1). This experiment confirmed the Western blots and demonstrated that SCPA$^-$ cultures lack other proteases which might degrade rhC5a.

Although M protein expression was not expected to be influenced by mutations in scpA, assays were performed to assess whether SCPA$^-$ mutant streptococci still expressed M protein and had the ability to resist phagocytosis. Growth of streptococci in fresh human blood during 3 hours incubation is indicative of antiphagocytic M protein on their surface. R. C. Lancefield, "Differentiation of Group A Streptococci with a Common R Antigen into Three Serological Types, with Special Reference to Bactericidal Test," *J. Exp. Med.*, 106, pp. 525–685 (1957). As expected, parent streptococci UAB200 and CS101 increased 40 and 49 fold, respectively (Table 1). The M$^+$ SCPA$^-$ cultures, strains AK1.4 and MJ3-15, increased 37.5 and 14-fold, respectively, confirming that scpA mutations had little effect on M protein expression or resistance to phagocytosis in whole human blood. The somewhat poorer growth of both mutant strains in rotated blood was reproducible and unexpected. The growth rates of mutant and parent cultures in human plasma were indistinguishable. It is possible that inactivation of SCPA allowed C5a to accumulate in rotated blood which in turn activated PMNs. Activated PMNs are more phagocytic and better able to kill M$^+$ streptococci. Surface protein extracts contain M6 and M49 antigen when analyzed by Western blot using anti-M49 and anti-M6 antisera, confining that mutations in SCPA did not alter M protein expression.

EXAMPLE 2

SCP Delays Recruitment of Phagocytes and Clearance of Streptococci from Subdermal Sites of Infection In order to verify that SCP was responsible for the inactivation of C5a, the insertion and deletion mutants of scpA49 were constructed as described in Example 1 above, and tested for activity. When insertions or deletions were introduced into scpA49, the variant SCP was not able to destroy C5a-activated adherence of PMNs to microtiter plates.

The impact of mutations in scpA49 on virulence was tested using an animal model where streptococci remained localized, and where the influx of inflammatory cells could be analyzed. To test the hypothesis that SCP functions very early to retard initial clearance of the organism, the fate of SCP$^+$ and SCP$^-$ streptococci just 4 hours after inoculation of connective tissue air sacs was compared. Moreover, the dissemination of streptococci to lymph nodes and spleens after this short period of infection was also assessed.

CD1 male outbred mice (25 g) obtained from Charles River Breeding Laboratory, Wilmington, Mass. were used for all experiments. A connective tissue air sac was generated by injecting 0.9 ml of air and 0.1 ml group A streptococci diluted in PBS with a 25-gauge needle under the skin on the back of the mouse. In some experiments the SCP$^+$ CS101::pG$^+$host5 was used as a positive control. In other experiments strain CS101Sm was used as the positive con-

TABLE 1

Phagocytosis assay and PMN adherence assay of wild-type and mutant strains

| Strain | Description | Colony forming units (cfu)/ml | | Fold increase in cfu/ml | Percent inhibition of C5a induced PMN adherence* |
|---|---|---|---|---|---|
| | | Time = 0 h | Time = 3 h | | |
| UAB200 | M6$^+$, SCPA$^+$ | 1.8 × 10$^3$ | 7.2 × 10$^4$ | 40 | 58.8 |
| AK1.4 | M6$^+$, SCPA$^-$ | 1.2 × 10$^3$ | 4.5 × 10$^4$ | 37.5 | 0 |
| CS101 | M49$^+$, SCPA$^+$ | 1.0 × 10$^4$ | 4.9 × 10$^5$ | 49 | 54.5 |
| MJ3-15 | M49$^+$, SCPA$^-$ | 1.5 × 10$^4$ | 2.1 × 10$^5$ | 14 | 0 |

*Percent inhibition = [($OD_{570\ nm}$ of PMNs activated by C5a alone − $OD_{570\ nm}$ PMNs activated by C5a preincubated with bacteria / $OD_{570\ nm}$ of PMNs activated by C5a alone)] × 100%.

trol. Mice were euthanized by cervical dislocation 4 hours after infection. Where indicated, all four inguinal lymph nodes, spleen and air sac were dissected from the animals and homogenized in PBS. Tissue suspensions were assayed for viable colony forming unit (CFU) on blood agar plates containing 1 µg/ml erythromycin or 200 µg/ml streptomycin.

In a preliminary experiment air sacs were fixed on slides, stained with Wright's stain and examined microscopically. Although counts of granulocytes by this method were unreliable, there appeared to be significantly fewer residual $SCP^-$ than wild-type streptococci in fixed tissue. Additional experiments were performed in an attempt to measure this difference. Dispersed cell populations of air sacs were prepared by grinding the air sac in PBS and passing them through Nylon monofilament mesh (TETKO Co. New York).

The cells were pelleted by centrifugation 5 min at 300×g and resuspended at $5 \times 10^6$/ml in FACS buffer (Hank's balanced salt solution without phenol red, 0.1% $NaN_3$, 1.0% BSA fraction V). Cells ($1.0 \times 10^6$) were stained directly with 1 µg FITC anti-mouse Mac-1 or indirectly with 1 µg Biotin conjugated anti-mouse Gr-1 followed by 1 g Streptavidin labelled with fluorescene or FITC. Monoclonal antibodies, Mac-1 and Gr-1, were obtained from Pharmingen, Inc. Calif. Labeled cells were fixed in 1.0% paraformaldehyde. Fluorescence profiles were generated using a FAC-Scan flow-cytometer and Consort 32 software (Becton Dickinson). Mouse PMNs were purified from whole blood by Ficoll Hypaque density gradient centrifugation and used as a standard to defined PMNs in mixed populations. For measurement of specifically labeled cells, the mean fluorescence for each antibody marker was determined and gates were set to reflect intensely labeled cells. Controls included unstained cells, and cells exposed to only streptavidin FITC.

Two experiments were performed. The first compared the scpA49 insertion mutant M16 to its $SCP^+$ parent culture, strain CS101. The second compared the scpA49 deletion mutant MJ3-15, to its parent, strain CS101Sm. (Table 2) In both experiments homogenized air sacs from mice inoculated with $SCP^-$ streptococci contained fewer numbers of streptococci than air sacs inoculated with wild-type streptococci. The first experiment showed a two-fold reduction and the second showed a four-fold reduction. These differences were statistically significant at P<0.05 and P<0.001, respectively, using an Unpaired t-test. It was also observed that wild-type $SCP^+$ streptococci were found in spleen homogenates from 7 of 8 mice and 6 of 8 mice; whereas, the $SCP^-$ mutants were rarely found in the spleen. The opposite was true for lymph node homogenates. Nodes from 10 of 16 mice infected with $SCP^-$ streptococci harbored viable streptococci; whereas, only 4 of 16 nodes from mice infected with wild-type streptococci contained viable bacteria. This difference was determined to be statistically significant at P<0.05 using the Fisher's exact test.

TABLE 2

Distribution of $SCP^+$ and $SCP^-$ streptococci
4 hours after air sac infection

| Strains | No. of Mice[a] | spleen[b] | lympyh node | Homogenized Air Sac[c] |
|---|---|---|---|---|
| CS101pG($SCP^+$) | 8 | 7 | 2 | $1.3 \times 10^8 \pm 2.2 \times 10^7$ |
| M16 ($SCP^-$) | 8 | 0 | 5 | $6.0 \times 10^7 \pm 1.3 \times 10^7$ |

TABLE 2-continued

Distribution of $SCP^+$ and $SCP^-$ streptococci
4 hours after air sac infection

| Strains | No. of Mice[a] | spleen[b] | lympyh node | Homogenized Air Sac[c] |
|---|---|---|---|---|
| CS101Sm ($SCP^+$) | 8 | 6 | 2 | $1.6 \times 10^8 \pm 2.6 \times 10^7$ |
| MJ3-15 ($SCP^-$) | 8 | 1 | 5 | $3.7 \times 10^7 \pm 1.5 \times 10^7$ |

[a]Each mouse was inoculated with $3 \times 10^8$ CFU of stationary phase streptococci.
[b]Difference in the frequency of isolation of $SCP^+$ streptococci from spleens relative to $SCP^-$ streptococci was statistically significant (P <0.05) for each experiment by the Fisher's exact test.
[c]Differences in CFU isolated from homogenized air sacs (means ± SEMs) were significant, strains CS101pG ($SCP^+$) and M16 ($SCP^-$) and MJ3-15 ($SCP^-$) (P <0.001) for each experiment by unpaired t test.

The more rapid clearance of streptococci from air sacs resulted from more intense recruitment of PMNs. The total cell population, the percentage of Mac-1 positive granulocytes (Springer, G. et al., "Mac-1: macrophage differentiation antigen identified by monoclonal antibody," *Eur. J. Immunol.* 9:301–306 (1979)), and the percentage of Gr-1 positive PMN (Brummer, E. et al., "Immunological activation of polymorphonuclear neutrophils for fungal killing: studies with murine cells and blastomyces dermatitis in vitro," *J. Leuko. Bio.* 36:505–520 (1984)) in air sacs were compared by single color FACS analysis. Clark, J. M., "A new method for quantitation of cell-mediated immunity in the mouse," *J. Reticuloendothel Soc.* 25:255–267 (1979). Briefly, in a FACS analysis, individual cells in suspension are labelled with specific fluorescent monoantibodies. Aliquots of labelled cells are injected into a FAC-Scan flow-cytometer or fluorescent cell sorter which counts cells based on their unique fluorescence.

Figure 4:
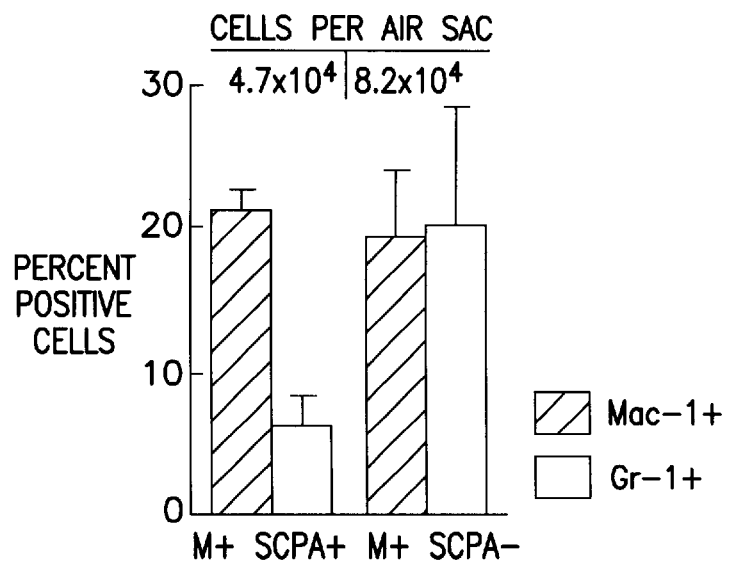
FIG. 4. Single color FACS analysis. Fluorescence data were analyzed by gating on PMNs. A second gate was set to count high staining cells defined by the first gate. Air sacs were inoculated with $1 \times 10^6$ CFU.

Air sacs infected with the $SCP^-$ deletion mutant contained twice as many inflammatory cells as those inoculated with $SCP^+$ streptococci (FIG. 4). A hundred-fold increase in the inoculum size did not alter this difference. Air sacs infected with $1 \times 10^6$ $SCP^-$ cells, strain MJ3-15, contained three times more Gr-1 positive cells than those inoculated with the $SCP^+$ culture. In airs sacs inoculated with $SCP^+$ streptococci approximately 6% of the cells were PMNs and 21% were other kinds of Mac-1$^+$ granulocytes, including PMNs. In contrast, air sacs inoculated with $SCP^-$ streptococci contained predominantly PMNs. Gr-1 positive cells were equal to or greater than the number of Mac-1 positive cells. Flow cytometer gates were set to measure only high staining granulocytes. The remaining 70–80% of cells not stained with either antibody were likely either low staining granulocytes, red blood cells or lymphocytes. Large numbers of lymphocytes were observed microscopically in Wrights stained air sac preparations.

$SCP^+$ colonies of streptococci that emerged from spleen homogenates were highly encapsulated, resembling water drops. In contrast the few $SCP^-$ colonies arising from lymph nodes, were more like the inoculum. They were mixtures of non-mucoid and moderately mucoid colonies. These data suggest that $M^+SCP^+$ encapsulated streptococci can adapt, multiply and invade the bloodstream within 4 hours after infection. The basis for differential trafficking of mutant and wild-type streptococci may be due to the more vigorous influx of phagocytic cells in response to $SCP^-$ bacteria. Macrophages and/or skin dendritic cells may more rapidly engulfed SCP streptococci and delivered them to lymph nodes. Reduction of mutant streptococci relative to wild-type is an unexpected finding, because $SCP^-$ streptococci are $M^+$ and resistant to phagocytosis by human neutrophils in vitro.

EXAMPLE 3

SCP Is Required for Colonization of the Mouse Nasopharynx

Mice were inoculated intranasally to evaluate the relative capacity of wild-type (SCP$^+$) and SCP$^-$ streptococci to colonize the nasopharynx. Streptomycin resistant M49 strain CS101 and deletion mutant MJ3-15 were used in these experiments. Cultures were not mouse passed in order to avoid selection of variants that might be uniquely mouse virulent, but no longer depend on M protein and/or SCP for persistence in the animal.

Sixteen hour cultures of challenge streptococcal strains ($1 \times 10^8$–$9 \times 10^8$ CFU), grown in Todd-Hewitt broth containing 20% normal rabbit serum and resuspended in 10 µl of PBS, were administered intranasally to 25 g female CD1 (Charles River Breeding Laboratories, Inc., Wilmington, Mass.) or BALB/c mice (Sasco, Omaha Nebr.). Viable counts were determined by plating dilutions of cultures on blood agar plates. Throat swabs were taken daily from anesthetized mice for 6 to 10 days after inoculation and streaked onto blood agar plates containing 200 ug/ml streptomycin. After overnight incubation at 37° C., the number of β-hemolytic colonies on plates were counted. All challenge strains were marked by streptomycin resistance to distinguish them from β-hemolytic bacteria which may be persist in the normal flora. Throat swabs were cultured on blood agar containing streptomycin. The presence of one β-hemolytic colony was taken as a positive culture.

Figure 5:
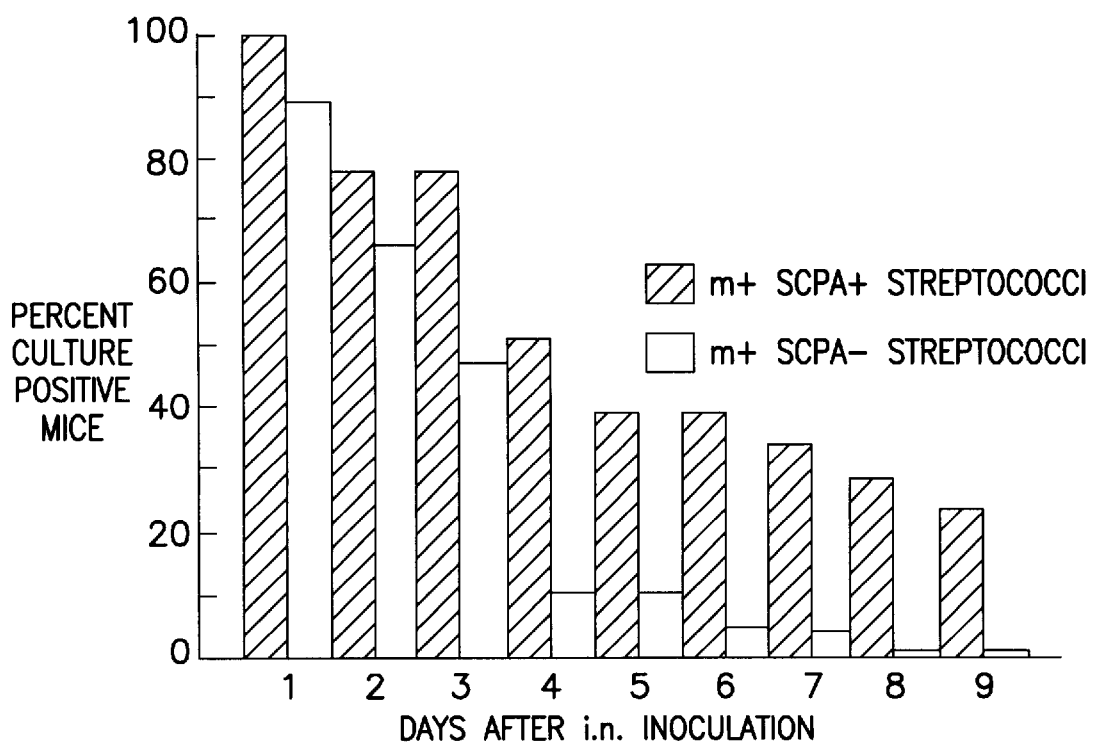
FIG. 5. Persistence of Wild-type and SCPA⁻ serotype M49 streptococci following intranasal infection.

CD1 outbred mice were intranasally inoculated with $2 \times 10^8$ stationary phase CFU. The nasopharynxes of anesthetized mice were swabbed daily for 8–10 days and streaked on blood agar containing streptomycin. Differences between SCP$^+$ and SCP$^-$ were evident by day 1, however, statistically significant differences were not observed until days 3 and 4 (FIG. 5). By day four 9/18 mice infected with M$^+$SCP$^+$ streptococci produced positive throat cultures, whereas only 2/18 mice infected with M$^+$SCP$^-$ strain retained streptococci in their throats. Four of 18 mice died from infection with SCP$^+$ streptococci. None of the mice following infection with SCP$^-$ bacteria succumbed to the infection. The numbers of colonies on the blood agar plates were also consistent with more rapid clearance of SCP$^-$ streptococci. For example, on the third day cultures from seven mice contained >100 SCP$^+$ CFU, whereas, only one mouse inoculated SCP$^-$ streptococci contained >100 CFU.

Figure 6:
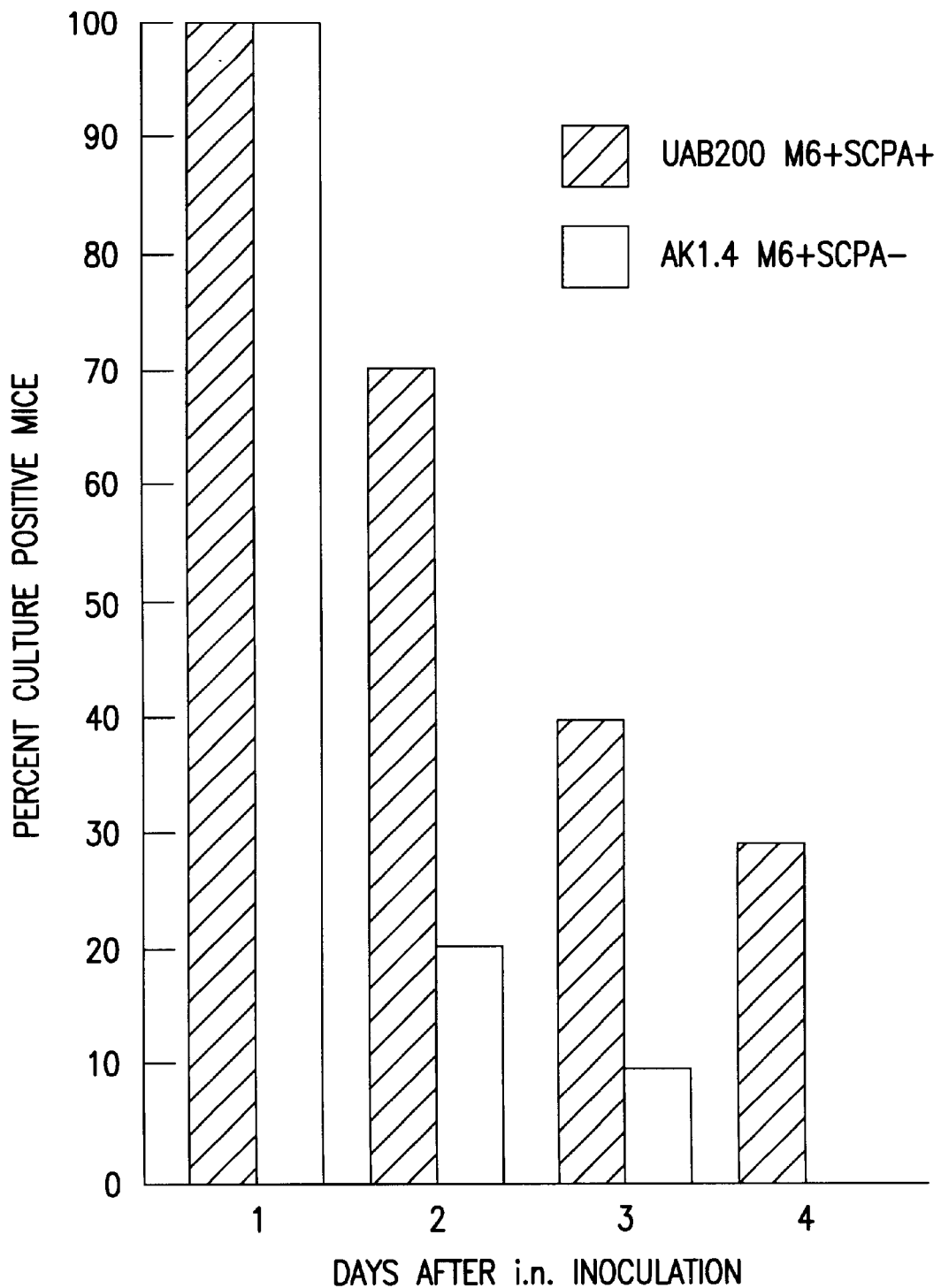
FIG. 6. Comparison of the ability of SCPA⁻ mutants of serotype M6 Group A streptococcus to colonize mice following intranasal infection. Compares BALB/c mice (ten in each experimental group) inoculated with $2 \times 10^7$ CFU of M6 streptococci. Throat swabs were cultured each day on blood agar plates containing streptomycin. Mice were considered positive if plates contained one β-hemolytic colony. Data were analyzed statistically by the $\chi^2$ test.

Because M49 streptococci are more often associated with skin infections the above experiments were repeated with an M6 strain, a serotype more often associated with throat infections. An insertion mutant, strain AK1.4, was constructed using the M6 strain UAB200 and the strategy previously described in Example 1. Strain AK1.4 was also cleared more rapidly than the wild-type M6 culture from the nasopharynx. (FIG. 6) The above experiments confirm that group A streptococci are dependent upon SCP for persistence in the mouse nasopharynx. All SCP$^-$ variants used in the above experiments were M$^+$, i.e. they resisted phagocytosis by fresh human blood. Yet, they were cleared from the nasopharyngeal mucosa.

EXAMPLE 4

Intranasal Immunization of Mice with Purified Recombinant SCPA49 Blocks Colonization Following Intranasal Challenge a) Construction of recombinant vaccine ΔSCPA49 encoding Thr$^{63}$ through His$^{1031}$ (FIGS. 2 and 7).

A PCR fragment which corresponds to a truncated form of the scpA49 gene was cloned from CS101 M49 group A streptococci (ΔSCPA49). This fragment was amplified by PCR using a forward primer beginning at nucleotide 1033 and a reverse primer beginning at nucleotide 3941 (numbering corresponding to that of Chen, C., and Cleary, P., "Complete nucleotide sequence of the streptococcal C5a peptidase gene of *Streptococcus pyogenes*," *J. Biol. Chem.* 265:3161–3167 (1990)). The fragment was ligated to the thrombin binding site of glutathione transferase gene on the pGex-4T-1 high expression vector from Pharmacia Inc. The plasmid containing the recombinant scpA fragment, designated pJC6, has been deposited in the American Type Culture Collection, Rockville, Md., under the provision of the Budapest Treaty, and assigned ATCC accession number 98225.

The ΔSCPA49, a 2908 bp fragment of scpA49, was amplified by PCR using an scpA49 forward primer containing a BamHI recognition sequence (5'-CCCCCC GGATCCACCAAAACCCCACAAACTC-3') (SEQ. ID. NO: 8) and an scpA reverse primer (5'-GAGTGGCCCTCCAATAGC-3') (SEQ. ID. NO: 9). Sequences which code for the signal peptide and membrane anchor regions of the SCPA protein were deleted from the resulting PCR product. PCR products were digested with BamHI and ligated to BamHI and SmaI restriction sites in the thrombin recognition site of the glutathione S-transferase gene on the pGEX-4T-1 high expression vector from Pharmacia Inc. (Piscataway, N.J.). The recombinant plasmid was transformed into *E. coli* DH5α. The ΔSCPA49 fusion protein from one transformant, *E. coli* (pJC6), was purified by affinity chromatography on a glutathione Sepharose 4B column. The transferase-SCP fusion protein from one *E. coli* clone was expressed and purified by affinity chromatography on a glutathione Sepharose 4b column. All methods are described by the manufacturer (Pharmacia). The ΔSCPA49 was cleaved from the hybrid protein by thrombin digestion. The thrombin was removed from eluted SCP by chromatography on a benzamidine Sepharose 6B column (Pharmacia). Following digestion with thrombin, thrombin was removed by chromatography on a benzamidine-Sepharose 6B column. Methods of expression and purification are described by the manufacturer. The affinity purified protein was confirmed to be pure ΔSCPA49 by SDS-PAGE and by Western blot. This affinity purified, truncated ΔSCPA49 protein lacked peptidase activity when tested by the PMN adherence assay (described in Example 1 above). Hyperimmune antiserum, directed against purified ΔSCPA49 was prepared in rabbits.

b) Immunization and challenge protocol. Four week old, outbred, CD1 female mice were immunized by administration of 20 µg of affinity purified ΔSCPA49 in 10 µl PBS into each nostril. Mice were immunized 3 times on alternating days and boosted again three weeks after the third immunization. After two weeks rest, mice were again boosted. D. Bessen et al., "Influence of Intranasal Immunization with Synthetic Peptides Corresponding to Conserved Epitopes of M Protein on Mucosal Colonization by Group A Streptococci," *Infect. Immun.* 56, pp. 2666–2672 (1988). Control mice received only PBS. Prior to infection, all mice which were immunized with ΔSCPA49 protein were determined by ELISA to have high titers of antibodies against ΔSCPA49 antigen in their serum and saliva. Group A streptococci, strain CS101 ($2.0 \times 10^8$ CFU), CS210 ($3.6 \times 10^8$ CFU), CS463 (7.8×10⁸ CFU), 90–131 (3.4×10⁸ CFU), and UAB200 (9.6×10⁸ CFU) were used to intranasally challenge the mice 7 days after the last vaccine booster. Animal studies were performed according to National Institutes of Health guidelines.

c) Sample collection and ELISA. Blood and saliva samples were collected from anesthetized mice after immunization. All sera were tested for the presence of SCPA49 antibodies by ELISA, as previously described. S. P. O'Connor et al., "The Human Antibody Response to Streptococcal C5a Peptidase," *J. Infect. Dis.*, 163, pp. 109–116 (1990). Purified SCPA49 protein was bound to microtiter wells by addition of 500 ng of purified protein in 0.05M bicarbonate buffer (pH 9.6). After overnight incubation at 4° C. the wells were washed, then blocked with 0.5% BSA in PBS for 1 hour. Salivation was stimulated in mice by injection of 100 µl of a 0.1% pilocarpine (Sigma) solution subcutaneously. Saliva samples were collected and spun at 14,000 rpm for 5 min in an Eppendorf microcentrifuge. The supernatants were tested for the presence of secretory IgA against ΔSCPA49 protein by ELISA. ELISA titers represent the highest dilution of individual serum and saliva which had an $OD_{405} \geq 0.1$.

d) Evaluation of Antibody Response to ΔSCPA49

Figure 8:
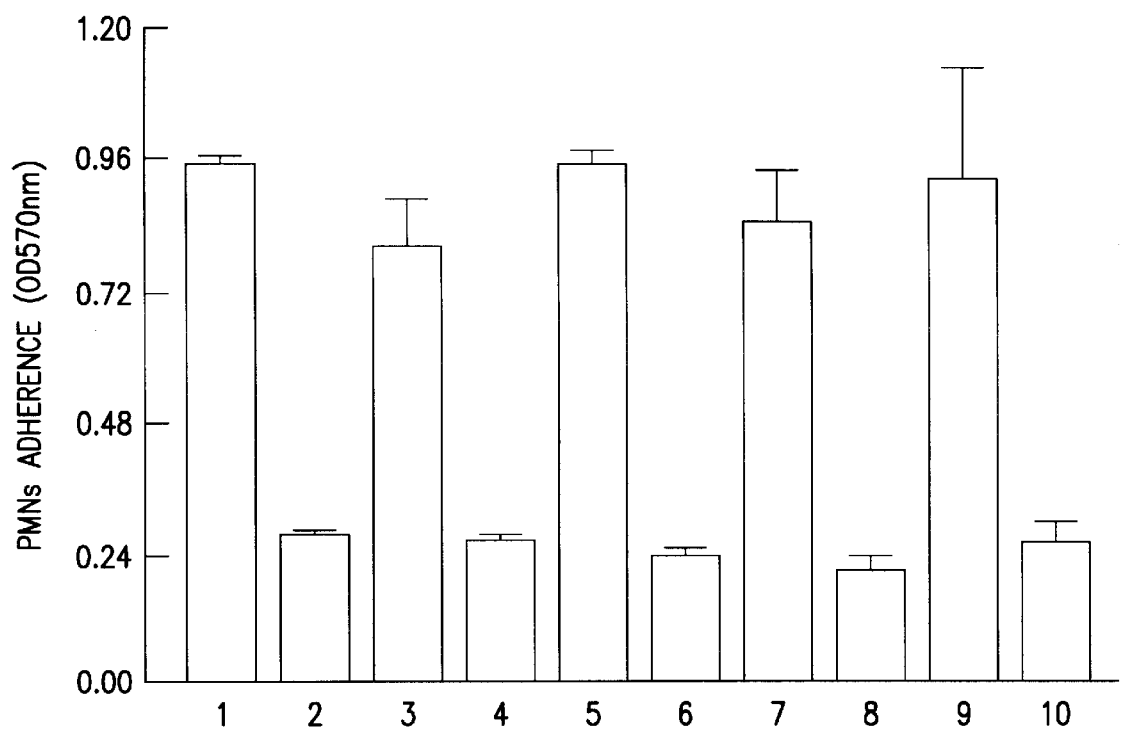
FIG. 8. Rabbit antibody neutralizes SCPA activity associated with different serotypes. Bar 1 is a positive control and contained rhC5a which was not preincubated before exposure to PMNs. Bar 10 is a control which lacks rhC5a. Whole, intact bacteria, preincubated with normal rabbit serum (bar 2, M1 90-131; bar 4, M6 UAB200; bar 6, M12 CS24; bar 8, M49 CS101) or preincubated with rabbit anti-SCPA49 serum (bar 3, M1 90-131; bar 5, M6 UAB200; bar 7, M12 CS24; bar 9, M49 CS101), were incubated with 20 μl of 5 μM rhC5a for 45 minutes. Residual rhC5a was assayed by its capacity to activate PMNs to adhere to BSA-coated microtiter plate wells. Adherent PMNs were stained with crystal violet.

The immunogenicity of the subunit ΔSCPA49 vaccine was evaluated. Rabbits were immunized with purified ΔSCPA49. The rabbits developed high levels of antibodies against ΔSCPA49 protein as determined by ELISA. Although the purified ΔSCPA49 immunogen lacked functional activity, hyperimmune rabbit antiserum could neutralize the peptidase activity of purified wild-type SCPA49 enzyme in vitro. Moreover, undiluted rabbit antiserum against ΔSCPA49 protein was able to neutralize C5a peptidase activity associated with different serotypes (FIG. 8). C5a peptidase activity associated with intact M1, M6 and M12 streptococci was inhibited by this antiserum, confirming that antibody against ΔSCPA49 protein lacks serotype specificity.

Figure 9A:
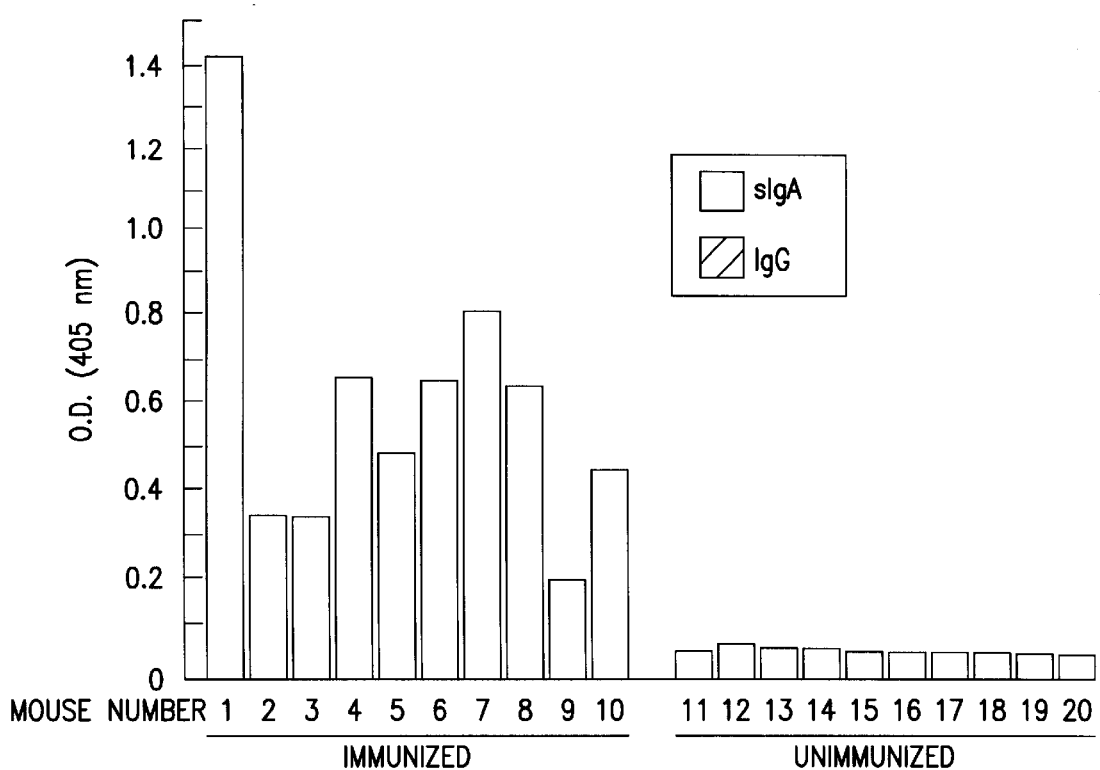
FIG. 9A shows the sIgA experimental results.
Figure 9B:
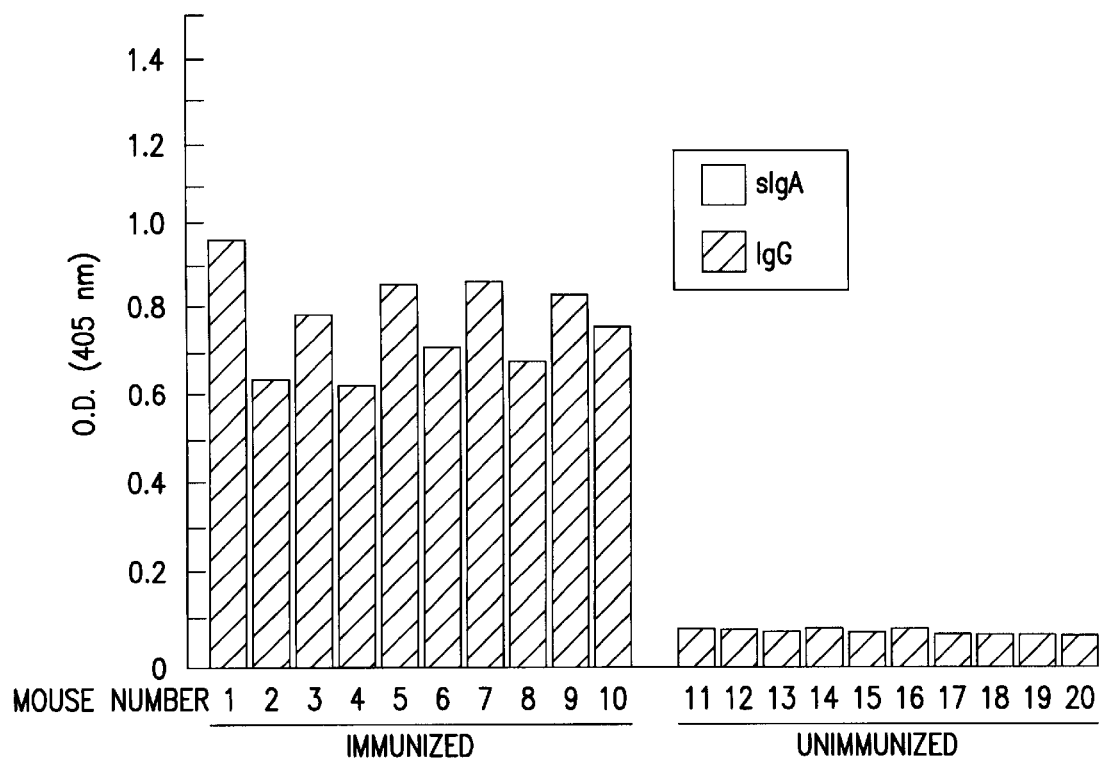
FIG. 9B shows the IgG experimental results.

Also, serum and saliva samples were obtained from ten immunized and ten control mice to assess the immunogenicity of ΔSCPA49 protein when administered via the intranasal route without adjuvants. Mice which were immunized with purified ΔSCPA49 protein developed high titers of ΔSCPA49-specific IgG in their sera, compared to control mice immunized with PBS (FIG. 9). Titers of serum IgG directed against ΔSCPA49 ranged from 1:10,240 to 1:20,480. In contrast, ΔSCPA49-specific IgG titer of control mice was not detectable in sera. Mice immunized with purified ΔSCPA49 protein also showed a significant increase in ΔSCPA49-specific salivary sIgA relative to control mice. Specific sIgA titers in saliva of immunized mice were greater than 1:16. In contrast, sIgA directed against ΔSCPA49 in the saliva of control mice was not detectable. The relative concentration of IgG and sIgA in serum diluted 1/2560 and saliva diluted 1/2, respectively, are shown in FIG. 9. These results demonstrate that purified ΔSCPA49 protein is an effective immunogen for the induction of specific systemic and secretory antibody responses in mice when administered intranasally.

e) Impact of vaccine ΔSCPA49 on Clearance of Streptococci from Infected Mice.

Figure 10B:
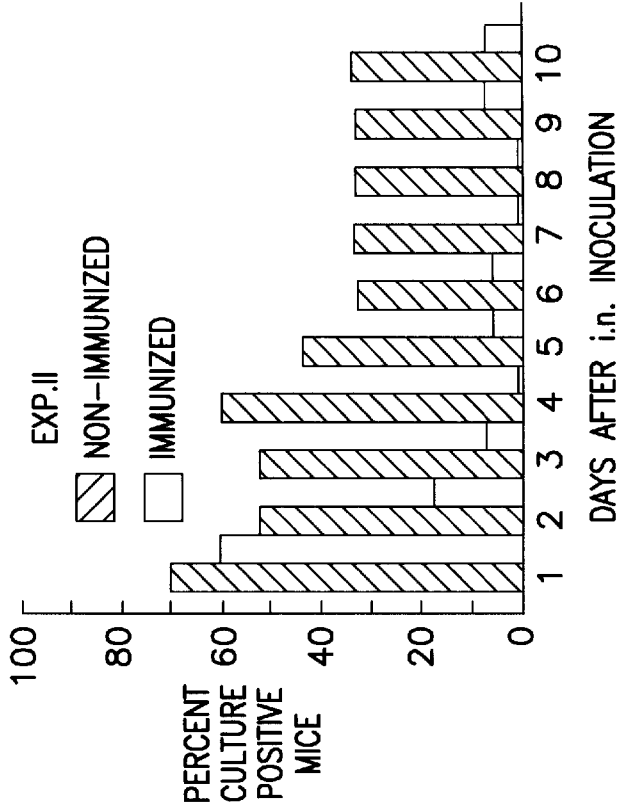
FIGS. 10A and 10B show the results of the repeated experiment.
Figure 10A:
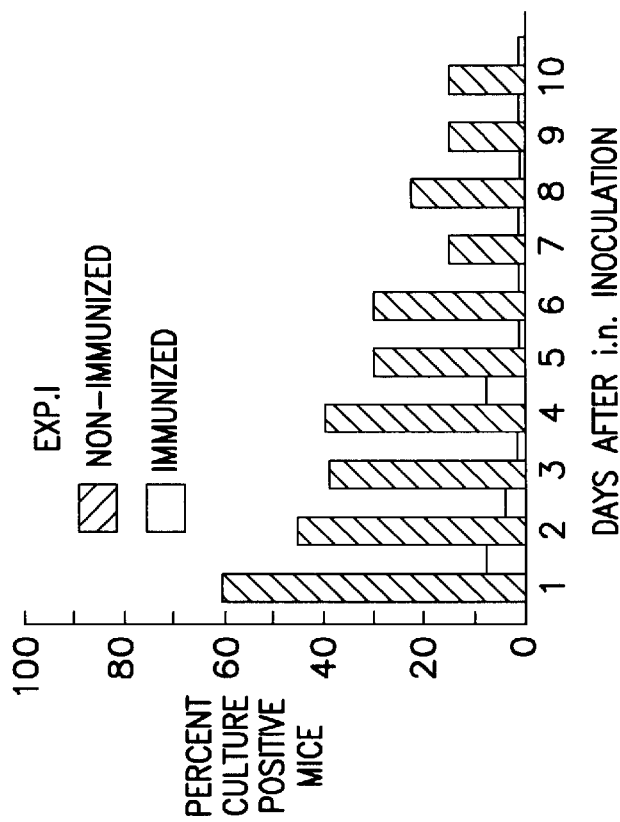

Experiments were performed to determine whether immunization with the C5a peptidase would enhance clearance of streptococci from the nasopharynx. Both hyperimmune rabbit and human sera that contain high levels of anti-SCPA antibody can neutralize SCPA activity in vitro. S. P. O'Connor et al., "The Human Antibody Response to Streptococcal C5a Peptidase," *J. Infect. Dis.*, 163, pp. 109–116 (1990). The fact that SCPA significantly facilitates colonization of the oral mucosa suggests that immunization of mice with purified ΔSCPA49 could reduce the capacity of streptococci to colonize the nasopharynx. Mice were immunized intranasally with affinity purified, genetically inactivated SCPA to test this possibility. The truncated protein, ΔSCPA49, was administered intranasally without adjuvants or carriers. Pharyngeal colonization of vaccinated mice by wild-type M⁺ SCPA⁺ streptococci differed significantly from those immunized with PBS in three independent experiments using mice vaccinated with two different preparations of purified ΔSCPA49 protein (Tables 3 and 4; FIG. 10). Only one of 13 mice immunized with ΔSCPA49 protein was culture positive for streptococci ten days after inoculation (Table 4; FIG. 10). In contrast, 30–58% of the non-vaccinated controls remained culture positive for six days, and some were still positive ten days after infection. The numbers of β-hemolytic, streptomycin resistant colonies on blood agar plates also showed a significant difference between ΔSCPA49 vaccinated and control mice. Different sets of immunized mice cleared serotype M49 streptococci significantly more rapidly from their nasopharynx than non-immunized control.

TABLE 3

Throat cultures for streptococci after intranasal challenge of mice vaccinated intranasally with PBS or SCP expressed in *E. coli* DH5α (CFU after vaccine)

| | Days after challenge | | | | | | | | | |
|---|---|---|---|---|---|---|---|---|---|---|
| Mice | 1 | 2 | 3 | 4 | 5 | 6 | 7 | 8 | 9 | 10 |
| PBSCT-II | | | | | | | | | | |
| 1 | 0 | 0 | 0 | 0 | 0 | 0 | 0 | 0 | 0 | 0 |
| 2 | 3 | 0 | 0 | 0 | 0 | 0 | 0 | 0 | 0 | 0 |
| 3 | 77 | >200 | 150 | 4 | 11 | 3 | 0 | 51 | 97 | 53 |
| 4 | 9 | >200 | >200 | 3 | 11 | 3 | 0 | 0 | 0 | 0 |
| 5 | 0 | 0 | 0 | 0 | 0 | 0 | 0 | 0 | 0 | 0 |
| 6 | 4 | 6 | 45 | 47 | 3 | >200 | 29 | >200 | 83 | 70 |
| 7 | 15 | 194 | >200 | 9 | 172 | 10 | 5 | 3 | 0 | 0 |
| 8 | 0 | 0 | 0 | 0 | 0 | 0 | 0 | 0 | 0 | 0 |
| 9 | 0 | 32 | 4 | 4 | 0 | 0 | 0 | 0 | 0 | 0 |
| 10 | 2 | 0 | 0 | 0 | 0 | 0 | 0 | 0 | 0 | 0 |
| 11 | 3 | 0 | 0 | 0 | 0 | 0 | 0 | 0 | 0 | 0 |
| 12 | 0 | 0 | 0 | 0 | 0 | 0 | 0 | 0 | 0 | 0 |
| 13 | 127 | 4 | 0 | 0 | 0 | 0 | 0 | 0 | 0 | 0 |
| No. of positive | 8 | 6 | 5 | 5 | 4 | 4 | 2 | 3 | 2 | 2 |
| SCPAD-II | | | | | | | | | | |
| 1 | 0 | 0 | 0 | 0 | 0 | 0 | 0 | 0 | 0 | 0 |
| 2 | 0 | 0 | 0 | 0 | 0 | 0 | 0 | 0 | 0 | 0 |
| 3 | 0 | 0 | 0 | 0 | 0 | 0 | 0 | 0 | 0 | 0 |
| 4 | 0 | 0 | 0 | 0 | 0 | 0 | 0 | 0 | 0 | 0 |
| 5 | 35 | 0 | 0 | 0 | 0 | 0 | 0 | 0 | 0 | 0 |
| 6 | 0 | 0 | 0 | 0 | 0 | 0 | 0 | 0 | 0 | 0 |
| 7 | 0 | 0 | 0 | 0 | 0 | 0 | 0 | 0 | 0 | 0 |
| 8 | 0 | 0 | 0 | 0 | 0 | 0 | 0 | 0 | 0 | 0 |
| 9 | 0 | 0 | 0 | 0 | 0 | 0 | 0 | 0 | 0 | 0 |
| 10 | 0 | 0 | 0 | 0 | 0 | 0 | 0 | 0 | 0 | 0 |
| 11 | 0 | 0 | 0 | 21 | 0 | 0 | 0 | 0 | 0 | 0 |
| 12 | 0 | 0 | 0 | 0 | 0 | 0 | 0 | 0 | 0 | 0 |
| 13 | 0 | 0 | 0 | 0 | 0 | 0 | 0 | 0 | 0 | 0 |
| No. of positive | 1 | 0 | 0 | 1 | 0 | 0 | 0 | 0 | 0 | 0 |

TABLE 4

Throat cultures for streptococci after intranasal challenge of mice vaccinated intranasally with PBS or SCP expressed in *E. coli* DH5α (CFU after vaccine)

| | Days after challenge | | | | | | | | | |
|---|---|---|---|---|---|---|---|---|---|---|
| Mice* | 1 | 2 | 3 | 4 | 5 | 6 | 7 | 8 | 9 | 10 |
| PBSCT-I | | | | | | | | | | |
| 1 | 112 | 143 | 85 | 16 | 0 | 0 | 0 | 0 | 0 | 0 |
| 2 | 127 | 27 | 18 | 89 | 3 | 7 | 7 | 7 | 70 | 3 |
| 3 | >200 | >200 | >200 | >200 | >200 | >200 | >200 | 108 | >200 | 66 |
| 4 | 31 | 200 | 4 | 2 | 0 | 0 | 0 | 0 | 0 | 0 |
| 5 | 4 | 0 | 0 | 3 | 3 | 0 | 0 | 0 | 0 | 0 |
| 6 | 0 | 0 | 0 | 0 | 0 | 0 | 0 | 0 | 0 | 0 |
| 7 | >200 | >200 | 120 | 125 | 91 | 145 | >200 | >200 | >200 | 166 |
| 8 | 2 | 0 | 0 | 0 | 0 | 0 | 0 | 0 | 0 | 0 |
| 9 | 0 | 0 | 0 | 0 | 0 | 0 | 0 | 0 | 0 | 0 |
| 10 | 0 | 0 | 0 | 0 | 0 | 0 | 0 | 0 | 0 | 0 |
| 11 | 37 | >200 | 194 | 16 | >200 | 47 | >200 | 101 | >200 | >200 |
| No. of positive | 8 | 6 | 6 | 7 | 5 | 4 | 4 | 4 | 4 | 4 |
| SCPAD-I | | | | | | | | | | |
| 1 | 6 | 0 | 0 | 0 | 0 | 0 | 0 | 0 | 0 | 0 |
| 2 | 105 | 41 | 0 | 0 | 0 | 0 | 0 | 0 | 0 | 0 |
| 3 | 0 | 0 | 0 | 0 | 0 | 0 | 0 | 0 | 0 | 0 |
| 4 | 2 | 0 | 0 | 0 | 0 | 0 | 0 | 0 | 0 | 0 |
| 5 | 2 | 0 | 0 | 0 | 0 | 0 | 0 | 0 | 0 | 0 |
| 6 | 9 | 0 | 11 | 0 | 0 | 0 | 0 | 0 | 0 | 0 |
| 7 | 0 | 0 | 0 | 0 | 0 | 0 | 0 | 0 | 0 | 0 |
| 8 | 26 | 0 | 0 | 0 | 0 | 0 | 0 | 0 | 0 | 0 |
| 9 | 0 | 19 | 0 | 0 | 5 | 57 | 0 | 0 | 21 | 91 |
| 10 | 0 | 0 | 0 | 0 | 0 | 0 | 0 | 0 | 0 | 0 |
| 11 | 7 | 0 | 0 | 0 | 0 | 0 | 0 | 0 | 0 | 0 |
| No. of positive | 7 | 2 | 1 | 0 | 1 | 1 | 0 | 0 | 1 | 1 |

*Mice were inoculated twice, because the dose of bacteria was too low at first time inoculation.

Last, it was examined whether SCP of one serotype would vaccinate animals against infection from other serotypes. There are more than 80 different serotypes of group A streptococci. An effective vaccine should prevent infection to more than one streptococcal serotype. Cross-protection was produced against colonization by the streptococcal OF$^+$ serotype M2 and M11 and the OF$^-$ serotype M1 and M6. The fact that rabbit serum directed against ΔSCPA49 protein from serotype M49 streptococci neutralized peptidase activity associated with several serotypes suggested that intranasal immunization with a single subunit vaccine might reduce or eliminate pharyngeal colonization by those serotypes. To explore this possibility four groups of twenty mice were immunized by intranasal inoculation with affinity purified ΔSCPA49 protein as described above. Control mice received PBS. Prior to being challenged with streptococci, serum and saliva samples from randomly chosen, immunized and control mice were assayed for anti-SCPA antibody. All immunized mice tested had developed a strong serum and measurable salivary antibody response. Pharyngeal colonization of mice immunized with ΔSCPA49 protein by strains of all four serotypes was reduced relative to non-immunized controls. Differences were most significant on days 3 and 5 after inoculation (Table 5).

TABLE 5

Immune protectivity is serotype independent

| | Day 3 after inoculation | | | | Day 5 after inoculation | | | |
|---|---|---|---|---|---|---|---|---|
| | Nonimmune (+/total) | % | Immune (+/total) | % | Nonimmune (+/total) | % | Immune (+/total) | % |
| M2 | 10/19 | 52.6 | 2/19* | 10.5 | 3/19 | 15.8 | 1/19 | 5.2 |
| M11 | 17/20 | 85 | 11/20* | 55 | 8/20 | 40 | 2/20* | 10 |
| M1 | 16/19 | 84.2 | 11/19 | 57.9 | 7/19 | 37 | 2/19* | 10.5 |
| M6 | 14/20 | 70 | 12/19 | 63.2 | 8/20 | 40 | 4/19 | 21.1 |

+ means culture positive mice.
*Differences between immunized and non-immunized mice are statistically significant (P < 0.05). P values were calculated by $x^2$ analysis.

Statistically significant differences were observed between immunized and control mice inoculated with serotype M2, M11 and M1 strains. However, the OF⁺ serotypes M2 and M11 were more efficiently eliminated by immunized mice than were the OF⁻ strains, M1 and M6. M1 streptococcal colonization of immunized mice was significantly reduced relative to control mice. Only 10.5% of the immunized mice were culture positive by day 5 post-infection. In contrast, 37% of the control mice were culture positive with this strain. Although immunized mice appeared to clear M6 streptococci more rapidly, the differences were not statistically significant. As in previous experiments the number of β-hemolytic streptococcal colonies on blood agar plates were significantly fewer in samples taken from vaccinated mice than those taken from control animals. Thus, the ΔSCPA 49 protein was an effective vaccine that provided cross-protection against other streptococcal serotypes.

EXAMPLE 5

Site-directed Mutagenesis of SCPA49

Group A streptococcal serotypes can be divided into two major groups, OF⁺ and OF⁻ strains. The latter are more often associated with rheumatic fever and toxic shock, whereas OF⁺ strains are a common cause of impetigo and acute glomerulonephritis. Although the SCPA proteins of these groups are 95–98% identical, it is possible that the immune response to them may be somewhat different. This concern prompted efforts to develop defined variant SCPAs from an M1 OF⁻ strain and from an M49 OF⁺ strain in parallel. Amino acids that are required for catalytic activity were replaced with those expected to inactivate the enzyme (FIG. 1). The N and C-terminal amino acid boundaries of SCPA49, expressed the pGEX-4T-1 subclones, were $Asn^{32}$ and $His^{1139}$, respectively (FIGS. 1 and 8). $Ser^{512}$ (SCPA49S512A), $Asn^{295}$ (SCPA49N295A) and $Asp^{130}$ (SCPA49D130A) in the SCPA49 protein were replaced with Ala, and $Asn^{295}$ (SCPA49N295R) was replaced by Arg (Deborah Stafslicn, M. S. Thesis, University of Minnesota).

The method used to introduce mutations into the scpA49 gene from Streptococcus strain CS101 was the "megaprimer" method of site-directed mutagenesis. Barik, S., "Site directed mutagenesis in vitro megaprimer PCR," In: *Methods in Molecular Biology*, Vol. 57: In Vitro Mutagenesis Protocols, Humana Press, Inc. Totowa, N.J. (1996). The serine mutation was introduced using primers scpFor940 (5'-CCCCCCGGATCCAATACTGTG ACAGAAGACACTCC-3'), SEQ. ID. NO: 10, and scp-mutrev 883 (5'-TTTCTGGAACTAGTATGTCTGCGCC-3'), SEQ. ID. NO: 11, to amplify a 1450 bp double-stranded PCR product. This first PCR product, a "megaprimer," was purified using the Qiagen Qiaquick Gel Extraction Kit, then used in a second asymmetrical PCR reaction to amplify the 3.3 kb scpA49 gene containing the desired mutation. Five cycles of denaturation (93° C., 1 min) and extension (72° C., 5 min) were carried out before addition of the reverse primer scpRev4263, (3'-CCCCCCCTCGAGATGTAA ACGATTTGTATCCTTGTCATTAG-3') SEQ. ID. NO: 12. During the fifth cycle at 72° C., the reverse primer was added at a concentration of 1 mM. The amplification was completed using 25 cycles at 94° C. for 1 min, 58° C. for 2 min, and 72° C. for 2–3.5 minutes. Reactant concentrations were the same as described in the previous section, except that a forward primer was not added and the megaprimer was added at a concentration of 4–6 µg per 100 µl reaction. This process yielded variant protein SCPA49S512A (see Table 6 below).

The aspartate and asparagine variants were constructed in much the same fashion, using the reverse primers scp-mutrev717 (5'-CAGTGATTGATGCTGGTTTTGATAA-3') SEQ. ID. NO: 13 and scpmutrev1214 (5'-AGCTACTATCAGCACCAG-3') SEQ. ID. NO: 14 to construct 311 bp and 805 bp megaprimers, respectively. The primer scpmutrev717 was used to generate variant protein SCPA49D130A, and primer scpmutrev1214 was used to generate variant protein SCPA49N295A (see Table 6 below). After Qiaquick purification, however, the megaprimer was treated with 0.1 U mung bean nuclease (per 4 µg DNA) and incubated at 30° C. for 10 minutes. The nuclease was removed by phenol/chloroform extraction, and the mcgaprimer recovered in the aqueous phase by ethanol precipitation. The pellet was resuspended in 80 µl sterile double distilled water, and 37 µl of this was used in each 100 µl asymmetrical PCR reaction. The mutated gene was then cloned into pGEX 4T-1 as previously described. Sequencing of variants was performed using $^{35}$S-labeled dATP and the Sequenase kit (Stratagene) or using automated fluorescent sequencing at the University of Minnesota Microchcmical Facility.

TABLE 6

Amino acid sequence comparison of variant proteins

| | 127 | 132 | 291 | 297 | 508 | 514 | 876 | 883 |
|---|---|---|---|---|---|---|---|---|
| Wild-type SCPA49 | AVIDAG | | TSAGNDS | | LSGTSGT | | STLGSRF | |
| SCP 5512S49 | AVIDAG | | TSAGNDS | | LSGTAGT | | STLGSRF | |
| SCP D130A49 | AVIAAG | | TSAGNDS | | LSGTSGT | | STLGSRF | |
| SCP N295A49 | AVJDAG | | TSAGADS | | LSGTSGT | | STLGSRF | |

The *E. coli* expression vector pGEX 4T-1 was used to overexpress variant SCPA as GST fusion proteins. Recombinant SCPA was purified according to the protocol provided in the GST Gene Fusion System Handbook (Pharmacia) previous to this work. The SCPA protein antigen was purified by affinity chromatography as described above.

EXAMPLE 6

Construction of SCPA1 and SCPB Variants

The wild-type scpA1 gene was amplified by PCR from M1 serotype of *S. pyogenes* (strain 90–226) in the following manner. Primers were designed such that only a fragment of the complete gene would be expressed. This fragment corresponds to the start of the mature protein and terminates just before the cell wall associated domain residue $Asn^{32}$ through $Asp^{1038}$ (FIG. 2). The forward primer 5'-CCC CCC<u>GAATTC</u>ATTACTGTGACAGAAGACACTCC TGC-3' (SEQ. ID. NO: 15) anneals starting at base number 940 (numbering corresponding to that of Chen, C., and Cleary, P., "Complete nucleotide sequence of the streptococcal C5a peptidase gene of *Streptococcus pyogenes*," *J. Biol. Chem.*, 265:3161–3167 (1990). The opposing, reverse PCR primer, 5'-C C C C C CC<u>GGATCC</u>TTATTGTTCTGGTTTATTAGA GTG GCC-3' (SEQ. ID. NO: 16) anneals at base number 3954 just upstream of a region of DNA repeats. This repeat region of the protein is predicted to be the part that passes through, and then attaches to the peptidoglycan of the cell wall. The italicized region of each primer is additional sequence that has been added to the *S. pyogenes* sequence to enable the cloning process. The underlined region of the forward primer incorporates a EcoRI restriction site, the underlined portion of the reverse primer a BamHI site. The reverse primer also incorporates a stop codon (TAA) in frame of the gene that terminates translation.

The resultant PCR product corresponding to bases 940–3954 was cloned into an intermediate vector pCR2.1 (Invitrogen, Inc.) and transformed into E. coli Top10F cells (Invitrogen, Inc.). Plasmid DNA from an appropriate transformant was restricted with EcoRI and BamHI. The 3018 base fragment, containing the fragment of scpA1, was gel purified following standard procedures and ligated into the expression vector pTrc99a (Pharmacia) restricted with the same enzymes. This ligation was transformed into E. coli DH5α cells and a transformant was selected that contained the desired plasmid construction. The resultant plasmid places the PCR fragment of scpA1 behind a Shine-Dalgarno sequence and ATG start site, and is under the transcriptional control of the trc Promoter, that is inducible with the allolactose analogue IPTG.

Site-specific genetic variants of the wild-type scpA1 were constructed following a procedure described by C. L. Fisher and G. K. Pei, "Modification of a PCR-based site-directed mutagenesis method," *BioTechniques*, 23:570–574 (1997). The appropriate amino acid residues within SCPA1 important for protease activity were predicted by sequence comparisons to the family of subtilisin-like serine protcases. Siezen, R. J., et al., "Homology modeling and protein engineering strategy of subtilases, the family of subtilisin-like serine proteinases," *Protein Engineering*, 4:719–737 (1991); Chen, C., and Cleary, P., "Complete nucleotide sequence of the streptococcal C5a peptidase gene of *Streptococcus pyogenes*," *J. Biol. Chem.*, 265:3161–3167 (1990). Three residues, conserved amongst this family, are involved in the formation of the active site. In SCPA1, these correspond to the $Asp^{130}$, $His^{193}$, and $Ser^{512}$. Three sets of non-overlapping oligonucleotides were designed for use in PCR to alter each one of these amino acid residues. These oligonucleotides were designed to amplify away from each other on opposite strands of DNA. In each set, the 5' end of one of the primers would contain the codon cncoding one of these amino acids for mutation and this codon would be altered to encode an alanine. These three sets of primers are listed below; the codons that are changes are italicized.

D130A:
 Forward
  5'-ATT GCT GCT GGT TTT *GAT* AAA AAT CAT GAA GCG-3' (SEQ. ID. NO:17)
GAT codon change to GCT corresponds to an aspartate to alanine amino acid change.
 Reverse
  5'-CAC TGC AAC AAC AGT CCC-3' (SEQ. ID. NO:18)
H193A:
 Forward
  5'-GAG GCC GGC ACA *CAC* GTG-3' (SEQ. ID. NO:19)
CAC codon change to GCC corresponds to a histidine to alanine amino acid change.
 Reverse
  5'-TTG ATC GAC AGC GGT TTT ACC-3' (SEQ. ID. NO:20)
S512A:
 Forward
  5'-*ACT* GCT ATG TCT GCT CCA TTA G-3' (SEQ. ID. NO:21)
ACT codon change to GCT corresponds to a serine to alanine amino acid change.
 Reverse
  5'-TCC AGA AAG TTT GGC ATA CTT GTT GTT AGC C (SEQ. ID. NO:22)

These sets of PCR primers were used in three separate reactions. The template DNA was pLP605, which contained the wild-type scpA1 sequence. The PCR products were subsequently self-ligated and transformed into the E. coli strain Top10F' (Invitrogen, Inc.). Transformants were screened for the appropriate size and restriction pattern. The sequence change in the S512A variant destroys a unique SpeI restriction site so that this mutation could be identified directly by restriction analysis. All potential variants were confirmed by DNA sequencing. Subsequently, the D130A mutation was combined with the S512A mutation to form a double variant utilizing a unique PstI site between these two regions of the protein. The final alteration was to change the antibiotic selection from ampicillin to kanamycin by moving the variant scpA1 genes to a previously altered pTRC99a vector (Pharnacia, Inc.) containing the kanamycin gene.

A variant of SCPB protein was constructed using the method described above for SCPA1 mutants. The wild-type SCPB gene was cloned from group B streptococcus 78–471 (Typc IIa$^+$).

EXAMPLE 7

Analysis of Variant Proteins

Proteins expressed from each of the variant constructs were analyzed by SDS polyacrylamidc gel electrophoresis. The expected size of the protein is 121 kD, however, the proline-rich cell wall spanning domain at the carboxy terminus of the enzyme causes the protein to run slightly slower during SDS-PAGE. Therefore the apparent molecular weight is 130 kD when determined by SDS-PAGE. Since active SCP could be harmful to the host, it was important that the variant proteins lacked enzymatic activity. Two properties of the variant proteins were evaluated. The specific activities of the wild-type and variant proteins as determined by PMN adherence assay are compared in Table 7. These experiments indicated that the substituted amino acids reduced enzymatic activity by greater than 90%.

TABLE 7

PMN adherence assay determination of variant protease activity

| Protein | Activity (U/mg*$10^{-3}$) |
|---|---|
| Wild-type | 170 |
| SCPA49D130A | <20 |
| SCPA49N295A | <20 |
| SCPA49S512A | <20 |

Figure 11:
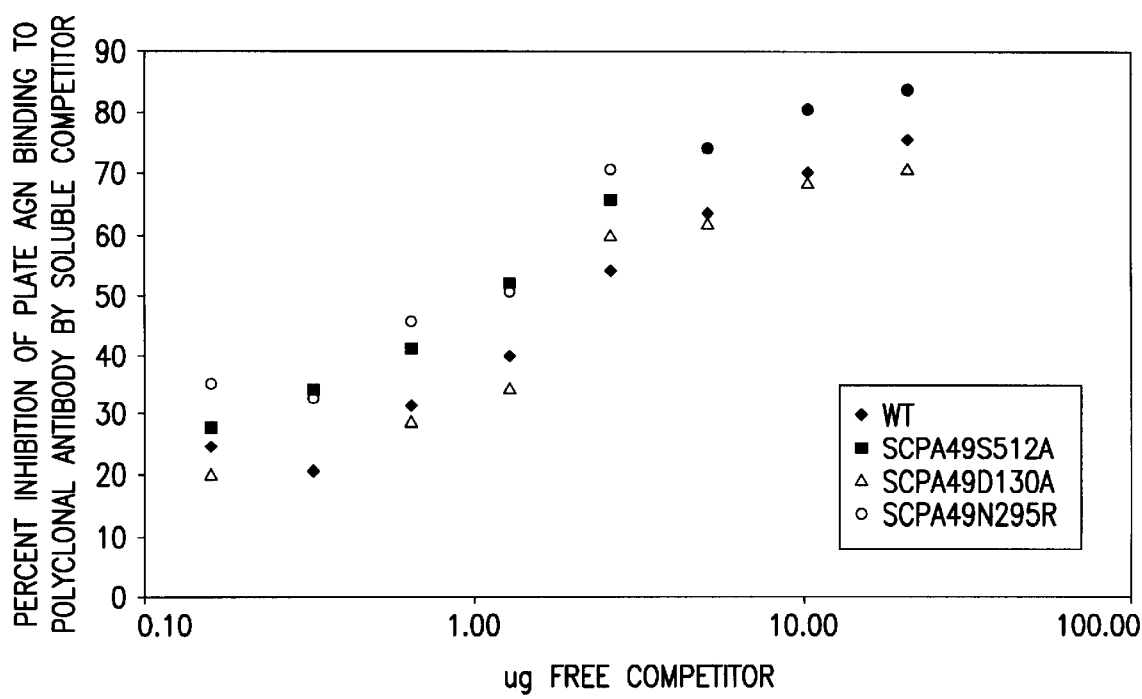
FIG. 11. Competitive ELISA Comparison of wild-type and variant SCP binding to polyclonal antibody. Plate antigen is recombinant wild-type SCPA49 (100 ng/well). Compacting antigen is indicated by the legend.

The variant proteins were also compared to the wild-type protein for their capacity to bind antibody directed against the wild-type enzyme. Competitive ELISA assays were used for this purpose. Competitive ELISAs measured the inhibition of antibody binding to immobilized antigen by soluble antigen. A constant amount of wild-type antigen was bound to wells of the microtiter plate. A constant amount of antibody is added at the same time with varying amounts of soluble competitive antigen. The slope of the percent inhibition versus antigen concentration curves estimate the relative binding affinity of the soluble antigen for antibody. While the binding conantnts cannot be calculated without knowing the exact concentration of anti-SCPA in the antiscim, the relative binding affinities of several proteins were compared (FIG. 11). Since the slopes of the percent inhibition versus concentration curves are the same for the wild-typc and variant proteins, it was concluded that amino acid substitution did not alter the ability of antibody to bind to the valiant proteins.

Figure 12:
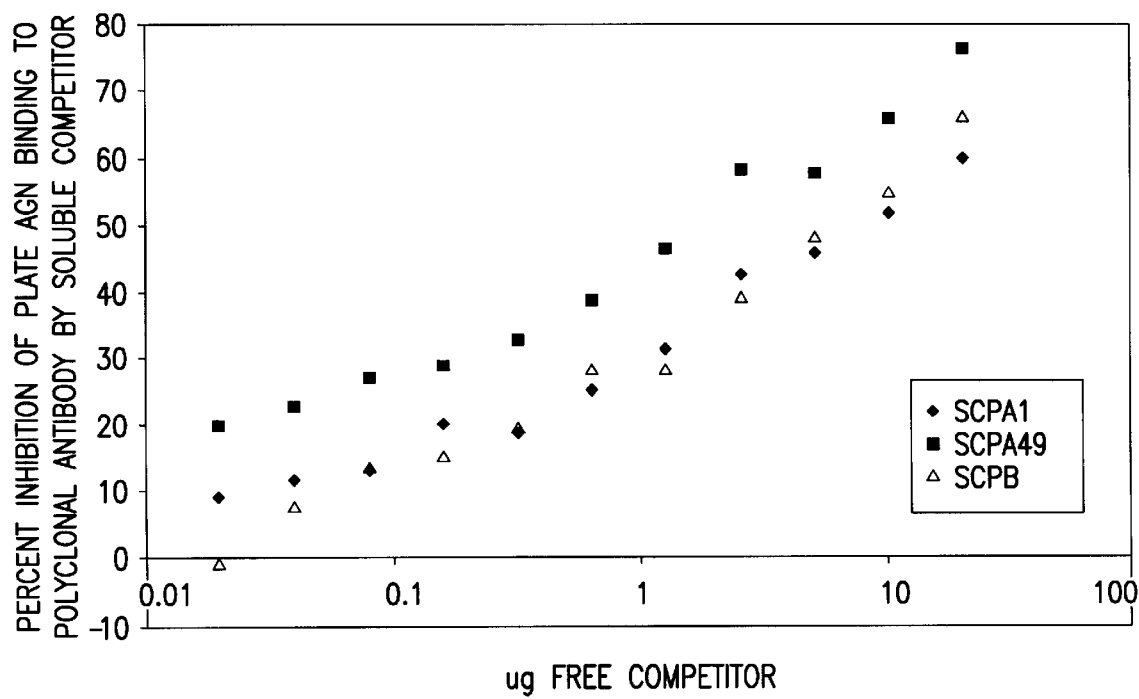
FIG. 12. Competitive ELISA Comparison of SCPA1, SCPA49 and SCPB binding to polyclonal antibody. Plate antigen is recombinant wild-type SCPA49 (100 ng/well). Competing antigen is indicated by the legend. SCPA1 and SCPA49 used in the experiments depicted in this Figure comprised $Asn^{32}$ through $His^{1139}$. SCPB used in the experiments depicted in this Figure was made according to Chmouryguina, I. et al., "Conservation of the C5a Peptidase Gene in Group A and B Streptococci", *Infect. Immun.*, 64:2387–2390 (1996).

Recombinant SCPA1, SCPA49 and SCPB proteins were also determined to bind equally well to anti-SCP antibody (FIG. 12). In this experiment the plate antigen was SCPA49 and the antibody was rabbit anti-SCPA49. The relative affinities of this antibody for these antigens, indicated by the slope of the curves is highly similar. These results demonstrate that SCPA protein from M49 OF⁺ and M1 OF⁻ group A Streptococci, and from group B streptococci are equivalent with regard to antibody recognition and may be used interchangeably in a vaccine preparation.

EXAMPLE 8

Subcutaneous (SQ) Administration of SCPA Antigen Induces Protection in Mice

All earlier protection studies were performed by administering affinity purified SCPA49 protein intranasally without adjuvant. Intramuscular or SQ injection of antigens is historically a preferred, more accepted method of vaccine delivery. Therefore, experiments were performed to test whether SQ injections of SCPA with MPL/alum induced a protective immune response and whether that response reduced colonization when the challenge strain of group A streptococcus differed in serotype from the source of the SCPA vaccine. The capacity of immunized mice to clear streptococci from the oral-nasal pharyngeal mucosa was evaluated by throat culture or by sampling dissected nasal tissue. Representative throat culture data are presented in Table 8.

TABLE 8

Subcutaneous vaccination of mice

| | | Percent Colonized[c] | |
|---|---|---|---|
| Vaccine[a] | Challenge Bacteria[b] | Control Mice | SPCA-Immunized Mice |
| SCPA49S512A | OF⁺M49 | 64% (3) | 36% |
| ΔSCPA49 | OF⁺M49 | 64% (3) | 20% |
| ΔSCPA49 | OF⁻M1 | 33% (5) | 8% |
| SCPA1S512A | OF⁻M49 | 23% (5) | 8% |

[a]Vaccines contained 10 μg of the indicated antigens mixed with adjuvants MPL and alum. Experimental groups each contained 13–20 mice. Control mice were immunized with tetanus toxoid mixed with the same adjuvant.
[b]Mice were infected by intranasal inoculation.
[c]Colonization was assessed by throat culture. The numbers in parentheses indicate the day on which the cultures were taken.

Mice immunized by SQ injection of each of the three different forms of SCPA antigen induced moderate protection. Immunization with ΔSCPA49 protected against both OF⁻ M1 and OF⁺ M49 strains. SCPA49S512A and SCPA1S512A were chosen for subsequent study.

Persistence of streptococci following intranasal challenge was also assessed by a more quantitative assay. This method involved sacrificing groups of mice at different times following infection, and dissecting nasal tissue (NT), which was then assayed for viable streptococci (CFU). Standard amounts of NT were homogenized in buffer and the number of CFU/mg tissue was determined by viable count.

Three groups of mice were immunized SQ with SCPA49S512A, SCPA1S512A or tetanus toxoid. All vaccines were mixed with MPL/Alum adjuvants as before. Mice received four injections of 5 μg protein antigen and then challenged two weeks after the last injection. Nasal tissue was harvested 16 hours after challenge with the OF⁺ M49 strain CS101. The geometric means of CFU/mg tissue are shown in Table 9.

TABLE 9

Geometric means of CFU/mg nasal tissue

| Vaccine Antigen | 16 hours[a] |
|---|---|
| Tetanus | 5.71[b] |
| SCPA49S512A | 2.27 |
| SCPA1S512A | 1.60 |

[a]The time at which NT was taken following intranasal infection of mice.
[b]Values are log values.

The number of streptococci associated with nasal tissue decreased with time, as expected and the decrease was more rapid and complete in mice immunized with SCPA antigen. All groups of mice that had been immunized with SCPA retained fewer streptococci than control mice. In this experiment immunization with SCPA1S512A was most effective and induced a cross-protective response, since the challenge strain CS101 is OF⁺ M49 and the source of vaccine protein SCPA1S512A from an OF⁻ M1 strain. These results confirm that a single SCPA antigen can induce protection against heterologous serotypes. Protection is afforded by antibody that neutralizes peptidase activity on the bacterial surface. This increases the influx of phagocytes within a few hours from the time streptococci are deposited on mucosal tissue. Rapid clearance of streptococci by phagocytes is presumed to prevent subsequent multiplication and persistence of the bacteria. Mice uniformly had serum IgG titers of 1:32,000 or greater when assayed by ELISA, indicating that SQ injection of SCPA antigen with adjuvant consistently induced a vigorous antibody response.

EXAMPLE 9

C5a Peptidase from Group B Streptococci Is Nearly Identical in Sequence to Those from M12 and M49 Group A Streptococci The group B streptococci C5a peptidase (SCPB) gene was cloned, sequenced and compared to that from serotype group A streptococci M12 and M49. The entire scpB gene was amplified by PCR using primers which correspond to portions of the scpA12 sequence using the method described above. The SCPB gene encodes an open reading frame (ORF) of 3450 bp which specifies a protein of 1150 amino acids with Mr of 126,237 da. The amino acid sequence of SCPB is shown in FIG. 2. Comparison of the scpB nucleotide and deduced amino acid sequence to those from M12 and M49 group A streptococci showed high similarities, 98% and 97%, respectively. ScpB contained a 50 bp deletion which overlapped two of the C-terminal repeats, and had several other minor differences relative to scpA genes. Alignment of the sequences showed that scpA12 is actually phylogenetically closer to scpB than it is to scpA49. Thirty strains, representing serotypes III, III/R, II, Ia/c, NT/c, NT/c/R1 carry a copy of scpB.

Recombinant SCP was expressed in E. coli using expression vector plasmid pGEX-4T-1 (ATCC accession number 98225) and was shown to be identical to the enzyme extracted from the parental group B streptococcal strain 78–471 (Type II a+b). Western blot analysis suggested the recombinant SCP is identical to the C5ase enzyme previously purified from group B streptococci.

All publications, patents and patent documents are incorporated by reference herein, as though individually incorporated by reference. The invention has been described with reference to various specific and preferred embodiments and techniques. However, it should be understood that many variations and modifications may be made while remaining within the scope of the invention.

What is claimed is:

1. A vaccine comprising an immunogenic amount of an enzymatically inactive streptococcal C5a peptidase (SCP), wherein the SCP is a variant of wild-type SCP, which amount is effective to immunize a susceptible mammal against β-hemolytic Streptococcus in combination with a physiologically-acceptable, non-toxic vehicle, wherein the SCP has a modification at one or more of amino acid residues 260, 261, 262, 415, 416, 417, 130, 193, 295 or 512.

2. The vaccine of claim 1 wherein the SCP is expressed from an isolated DNA sequence encoding SCP.

3. The vaccine of claim 1 wherein the SCP comprises a specificity crevice or catalytic domain.

4. The vaccine of claim 3 wherein the SCP comprises a specificity crevice.

5. The vaccine of claim 4 wherein the SCP comprises contiguous amino acid residues from about residue 260 to residue 417.

6. The vaccine of claim 1 wherein the modification is a substitution at one or more of amino acid residues 260, 261, 262, 415, 416, 417, 130, 193, 295 or 512.

7. The vaccine of claim 6 wherein the substitution is a conserved substitution.

8. The vaccine of claim 3 wherein the SCP comprises a catalytic domain.

9. The vaccine of claim 8 wherein the SCP comprises contiguous amino acid residues from about residue 130 to residue 512.

10. The vaccine of claim 8 wherein the SCP comprises one or more of amino acid residues 130, 193, 295 or 512.

11. The vaccine of claim 2 wherein the SCP is SCPA49D130A, SCPA49H193A, SCPA49N295A, SCPA49S512A, SCPA1D130A, SCPA1H193A, SCPA1N295A, SCPA1S512A, SCPBD130A, SCPBH193A, SCPBN295A, SCPBS512A or βSCPA49.

12. The vaccine of claim 11 wherein the SCP is SCPA1S512A.

13. The vaccine of claim 2 wherein the DNA encodes an SCP that does not contain a signal sequence.

14. The vaccine of claim 2 wherein the DNA encodes an SCP that varies from native SCP in that it does not contain a cell wall insert.

15. The vaccine of claim 1 wherein the vaccine comprises a variant of a streptococcal C5a peptidase that has reduced binding activity to C5a as compared to the binding activity of wild-type SCP to C5a.

16. The vaccine of claim 1 which further comprises an effective amount of an immunological adjuvant.

17. The vaccine of claim 1 wherein the mammal is a of human, dog, bovine, porcine or horse.

18. The vaccine of claim 17 wherein the mammal is human.

19. The vaccine of claim 1 wherein the β-hemolytic Streptococcus is a group A Streptococcus, group B Streptococcus, group C Streptococcus or group G Streptococcus.

20. The vaccine according to claim 19, wherein the β-hemolytic Streptococcus is Group A Streptococcus.

21. The vaccine of claim 1 wherein the SCP is a variant of SCP from group A Streptococcus, group B Streptococcus, group C Streptococcus or group G Streptococcus.

22. The vaccine according to claim 21, wherein the Streptococcus is Group A Streptococcus.

23. The vaccine of claim 1, which comprises a recombinant variant of a streptococcal C5a peptidase conjugated or linked to a peptide.

24. The vaccine of claim 1, which comprises a variant of a streptococcal C5a peptidase conjugated or linked to a polysaccharide.

25. The vaccine of claim 5 wherein the SCP has a modification at one or more of amino acid residues from 260 to residue 417.

26. The vaccine of claim 5 wherein the SCP has a modification at one or more of amino acid residues 260, 261, 262, 415, 416 or 417.

27. The vaccine of claim 9 wherein the SCP has a modification at one or more of contiguous amino acid residues from about residue 130 to residue 512.

28. The vaccine of claim 10 wherein the SCP has a modification at one or more of amino acid residues 130, 193, 295 or 512.

29. The vaccine of claim 25, 26, 27 or 28, wherein the modification is a substitution.

* * * * *

UNITED STATES PATENT AND TRADEMARK OFFICE
CERTIFICATE OF CORRECTION

PATENT NO. : 6,355,255 B1
DATED : March 12, 2002
INVENTOR(S) : P. Patrick Cleary and Deborah K. Stafslien It is certified that error appears in the above-identified patent and that said Letters Patent is hereby corrected as shown below:

<u>Column 60,</u>
Line 7, delete "of" between "a" and "human".

Signed and Sealed this

Thirteenth Day of August, 2002

Attest:

JAMES E. ROGAN
Attesting Officer     Director of the United States Patent and Trademark Office